(12) United States Patent
Kato et al.

(10) Patent No.: US 7,396,796 B2
(45) Date of Patent: Jul. 8, 2008

(54) TREATMENT AGENT, METHOD AND DEVICE FOR TREATING HAZARDOUS SUBSTANCES

(75) Inventors: Shinji Kato, Nagoya (JP); Hirokazu Watanabe, Nagoya (JP); Hisanori Kurobe, Nagoya (JP); Misao Iwata, Nagoya (JP); Koushi Yamaguchi, 14-16, Honcho 1-chome, Koganei-shi, Tokyo (JP) 184-0004

(73) Assignees: Noritake Co., Limited, Nagoya (JP); Koushi Yamaguchi, Tokyo (JP)

( * ) Notice: Subject to any disclaimer, the term of this patent is extended or adjusted under 35 U.S.C. 154(b) by 721 days.

(21) Appl. No.: 10/344,492

(22) PCT Filed: Oct. 3, 2001

(86) PCT No.: PCT/JP01/08705

§ 371 (c)(1),
(2), (4) Date: May 8, 2003

(87) PCT Pub. No.: WO02/34301

PCT Pub. Date: May 2, 2002

(65) Prior Publication Data

US 2003/0178296 A1     Sep. 25, 2003

(30) Foreign Application Priority Data

Oct. 20, 2000   (JP) ................. 2000-321552

(51) Int. Cl.
*B01J 31/00* (2006.01)
*B01J 23/00* (2006.01)
(52) U.S. Cl. .................... 502/152; 502/350
(58) Field of Classification Search ............ 502/350, 502/152
See application file for complete search history.

(56) References Cited

U.S. PATENT DOCUMENTS 5,779,912 A * 7/1998 Gonzalez-Martin et al. . 210/748

FOREIGN PATENT DOCUMENTS

| JP | 06-254139 | 9/1994 |
|---|---|---|
| JP | 08-023970 | 1/1996 |
| JP | 10-008376 | 1/1998 |
| JP | 10-204727 | 8/1998 |
| JP | 11-342316 | 12/1999 |
| JP | 2000-084361 | 3/2000 |
| JP | 2000-84361 A * | 3/2000 |
| JP | 2000-271444 | 10/2000 |

* cited by examiner

*Primary Examiner*—Jerry Lorengo
*Assistant Examiner*—Patricia L. Hailey
(74) *Attorney, Agent, or Firm*—Darby & Darby

(57) ABSTRACT

A hazardous substance treatment agent has a retainer and a transition metal oxide. The retainer has the specificity of retaining only a specific hazardous substance, such as a virus, a bacterium or a toxin, that has become mixed in or has the possibility of becoming mixed in a treatment subject, such as blood, that is in at least either a liquid or gaseous phase. By a photocatalytic action, the transition metal oxide inactivates said hazardous substance retained by the retainer.

22 Claims, 9 Drawing Sheets

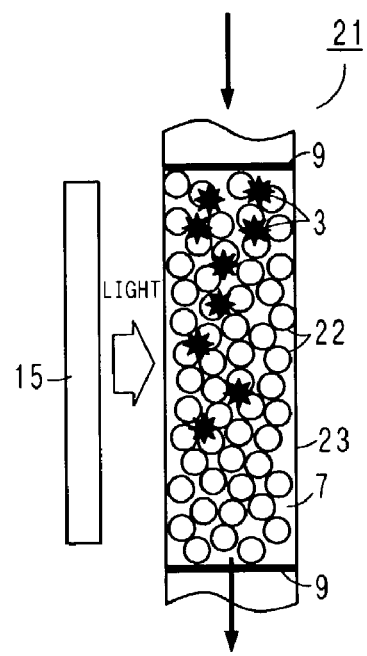
F I G. 7
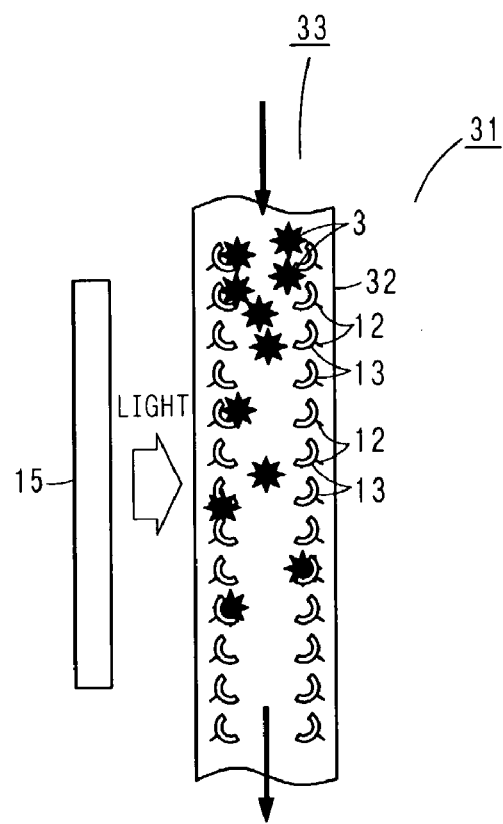
F I G. 8

TREATMENT AGENT, METHOD AND DEVICE FOR TREATING HAZARDOUS SUBSTANCES

This is a U.S. national phase application under 35 U.S.C. §371 of International Patent Application No. PCT/JP01/08705, filed Oct. 3, 2001, and claims the benefit of Japanese Patent Application No. 2000-321552, filed Oct. 20, 2000. The International Application was published in Japanese on May 2, 2002 as WO 02/34301 A1 under PCT Article 21(2).

TECHNICAL FIELD

The present invention relates to a hazardous substance treatment agent for inactivating a specific hazardous substance, such as a virus, a bacterium or a toxin. The invention also relates to a method of treating a hazardous substance and a device used for such a method.

BACKGROUND OF THE INVENTION

Examples of conventionally known methods of removing toxins or biologically hazardous organisms, such as viruses or pathogenic bacteria, from blood, a blood derivative or other similar matter in which such hazardous substances are contained include methods that call for heating organisms or toxins so as to kill, decompose or otherwise inactivate them, methods that call for mixing a photoactive pigment into the matter containing such a substance and inactivating the substance by irradiation with light, methods that call for inactivating hazardous substances by electrolysis, and methods that call for physically separating and removing hazardous substances with a filter.

However, methods that call for inactivating viruses, pathogenic bacteria or toxins by heat treatment present a problem in that the heat causes denaturation of not only the viruses, the pathogenic bacteria or the toxins but also constitutive proteins that constitute the blood or the blood derivative, and that complete inactivation of viruses, pathogenic bacteria or toxins inevitably requires heating conditions that are harsh to constitutive proteins. Methods that call for physical separation and removal of hazardous substances with a filter are often incapable of complete removal of viruses, pathogenic bacteria or toxins. As with methods using heat treatment, methods that call for electrolysis to inactivate viruses, pathogenic bacteria or toxins present the possibility of denaturation or decomposition of constitutive proteins together with the viruses, the pathogenic bacteria or the toxins and require harsher heating conditions to constitutive proteins to completely inactivate the viruses, the pathogenic bacteria or the toxins. These drawbacks of the individual methods have resulted in the present situation where a combination of different methods, for example heat treatment and separation removal using a filter, is usually employed, although the treatment process is complicated and time consuming.

Methods that call for mixing a photoactive pigment into blood and inactivating hazardous substances by irradiation with light involves mixing a pigment into blood or a blood derivative, which will enter a human body or the like. Therefore, it is necessary to choose a highly safe pigment that does not cause rejection symptoms. However, this results in various problems, including such complications as selecting pigments and confirming the safety of the pigments, limitations in usable pigments, and the limited range of use.

At present, when performing a clinical examination of drawn blood or body fluid, the blood or the body fluid itself does not undergo sterilization regardless of whether the subject is infected with any disease, because conventional sterilization for removing viruses or bacteria typically uses a chlorine-type disinfectant, an alkaline disinfectant or heat treatment and causes denaturation of components of the blood or the body fluid. In other words, conventional sterilization is effective when disposing such fluids but not suitable for preliminary treatment performed prior to a clinical examination. Therefore, when a clinical examination is conducted, sterilization treatment is not performed on the sample itself but only for protecting the handler of the sample from infectious diseases, i.e. what is generally called prevention of biohazard.

A semiconductor has the property of being energized, i.e. the state where electrons and pairs of holes are formed inside the semiconductor when irradiated with light having energy exceeding the band gap, i.e. the width of the forbidden band, of the material that constitutes the semiconductor. For example, titanium dioxide is energized by irradiation with long-wave ultraviolet or visible light and exhibits slight reduction capability and great oxidizing ability. As titanium dioxide is inorganic, it is completely harmless to the human body when it is not in the energized state. Because of this feature, titanium dioxide is used as an antiviral or antibacterial substance by using its great oxidizing ability, as is shown in, for example, Japanese Patent Provisional Publication Nos. 1994-254139, 1996-23970 and 2000-41667.

The conventional art disclosed in Japanese Patent Provisional Publication No. 1994-254139 calls for forming by thermal spraying a layer of composite ceramic on the surface of a base member to be exposed to a gas or a liquid, said composite ceramic consisting of a photo-semiconductor ceramic, such as titanium dioxide, and a ceramic having the adsorption capability, such as apatite. The base member is then brought into contact with a liquid or a gas so as to cause the ceramic having the adsorption capability to adsorb viruses and/or bacteria contained in the liquid or the gas, and light is radiated to the composite ceramic to inactivate the adsorbed viruses and/or bacteria.

The conventional art disclosed in Japanese Patent Provisional Publication No. 1994-254139, however, is not capable of effectively inactivating just bacteria or viruses, because there is the possibility of the ceramic having the adsorption capability also adsorbing components of the gas or the liquid, thereby undesirably causing denaturation or decomposition of the constitutive components.

The art disclosed in Japanese Patent Provisional Publication No. 1996-23970 calls for suspension dispersion of fine-grain photocatalyst made of titanium dioxide or other appropriate matter in a body fluid, such as blood, and inactivating viruses in the body fluid by irradiation with light.

However, the treatment process according to the method disclosed in Japanese Patent Provisional Publication No. 1996-23970 is complicated in that it requires a process of separating the titanium dioxide from the liquid. Furthermore, the method is not capable of effectively inactivating just viruses, because the strong oxidization capability of the titanium dioxide causes denaturation or decomposition of the constitutive components of the liquid, such as blood.

The art disclosed in Japanese Patent Provisional Publication No. 2000-41667 calls for supporting a photocatalyst made of, for example, titanium dioxide on the surface of a substance which will be exposed to blood or a blood derivative, and irradiating the photocatalyst with light so as to reduce through inactivation the infectivity of the viruses or the bacteria that have entered the blood or the blood derivative.

However, the method disclosed in Japanese Patent Provisional Publication No. 1996-23970, too, is incapable of effectively inactivating just infectious substances, such as viruses or bacteria, because the strong oxidization capability of the titanium dioxide causes denaturation or decomposition of the constitutive proteins in the blood or the blood derivative.

In other words, as is true in those disclosed in Japanese Patent Provisional Publication Nos. 1994-254139, 1996-23970 and 2000-41667, a method that calls for inactivating bacteria or viruses by using titanium dioxide, which shows the strong oxidization capability when irradiated with light, is incapable of effective treatment in that it denatures or decomposes not only substances to be inactivated, such as bacteria or viruses, but also constitutive components of the sample.

In order to solve the above problem, an object of the present invention is to provide a treatment agent, a method and a device for treating specific hazardous substances, such as viruses, bacteria or toxins by efficiently inactivating such hazardous substances.

DISCLOSURE OF THE INVENTION

A hazardous substance treatment agent according to the invention has a retainer and a transition metal oxide, wherein said retainer has the specificity of retaining only a specific hazardous substance that has become mixed in or has the possibility of becoming mixed in a treatment subject that is in at least either a liquid or gaseous phase, and said transition metal oxide is adapted to inactivate by a photocatalytic action the hazardous substance retained by said retainer.

Through the contact with the retainer, a specific hazardous substance that has become mixed in or has the possibility of becoming mixed in a treatment subject, which is in at least either a liquid or gaseous phase, is specifically retained by the retainer, and the hazardous substance retained by the retainer is inactivated by the photocatalytic function of the transition metal oxide. Therefore, the present invention is capable of efficiently inactivating a specific hazardous substance while inhibiting photocatalytic denaturation of the constitutive components of the treatment subject, thereby increasing the efficiency in treating the hazardous substance.

A hazardous substance treatment agent according to another feature of the invention is characterized in that the retainer is attached to the transition metal oxide.

Attaching the retainer to the transition metal oxide facilitates the separation of the retained hazardous substance alone from the treatment subject and the subsequent inactivation of the hazardous substance, and also permits the hazardous substance to be retained in the proximity of the transition metal oxide and efficiently inactivated. Thus, the treatment efficiency in selectively inactivating a hazardous substance separated from the treatment subject is increased.

A hazardous substance treatment agent according to yet another feature of the invention includes a base, and the transition metal oxide is provided on at least a part of the surface of said base.

Providing the transition metal oxide on at least a part of the surface of the base not only makes it possible to just provide the absolute minimum required transition metal oxide that contributes to the photocatalytic action, thereby reducing production costs, but also expands the range of usage, because the treatment agent can be applied to various usages by merely changing the form of the base according to conditions in which the agent is used or the criteria for treatment.

According to yet another feature of the invention, the base is formed of a translucent material.

Using a base formed of a translucent material increases the flexibility of radiation of light for development of the photocatalytic function, thereby expanding the range of usage.

According to yet another feature of the invention, the retainer of the hazardous substance treatment agent has amino groups, and the treatment agent includes bridge portions that are intended to bond to the transition metal oxide and include at the ends thereof aldehyde groups for bonding to said amino groups.

Attaching the retainer to the transition metal oxide through the bridge portions, which are intended to bond to the transition metal oxide and include at the ends thereof aldehyde groups for bonding to amino groups of the retainer, ensures that a retainer having the specificity of retaining only a specific hazardous substance is attached to a transition metal oxide having the photocatalytic ability, enables the easy achievement of both the ability of selective retention of a specific hazardous substance and the photocatalytic ability, and also increases the treatment efficiency in inactivating the hazardous substance while inhibiting photocatalytic denaturation of the constitutive components of the treatment subject.

According to yet another feature of the invention, the retainer of the hazardous substance treatment agent is a protein, and the treatment agent includes bridge portions intended to bond to the transition metal oxide and including at the ends thereof aldehyde groups for bonding to amino groups that constitute a protein.

Attaching the retainer to the transition metal oxide through the bridge portions, which are intended to bond to the transition metal oxide and include at the ends thereof aldehyde groups for bonding to amino groups constituting a protein of the retainer, ensures that a retainer having the specificity of retaining only a specific hazardous substance is attached to a transition metal oxide having the photocatalytic ability, enables the easy achievement of both the ability of selective retention of a specific hazardous substance and the photocatalytic ability, and also increases the treatment efficiency in inactivating the hazardous substance while inhibiting photocatalytic denaturation of the constitutive components of the treatment subject.

According to yet another feature of the invention, the bridge portions of the hazardous substance treatment agent are formed by bonding aminoalkylethoxysilane to the transition metal oxide and bonding glutaraldehyde to the amino groups of the aminoalkylethoxysilane bonded to the transition metal oxide.

Forming the bridge portions by bonding aminoalkylethoxysilane to the transition metal oxide and bonding glutaraldehyde to amino groups of the aminoalkylethoxysilane bonded to the transition metal oxide ensures that a retainer having the specificity of retaining only a specific hazardous substance is attached to a base having the photocatalytic ability, enables the easy achievement of both the ability of selective retention of a specific hazardous substance and the photocatalytic ability, and also increases the treatment efficiency in inactivating the hazardous substance while inhibiting photocatalytic denaturation of the constitutive components of the treatment subject.

According to yet another feature of the invention, the bridge portions of the hazardous substance treatment agent are formed by reducing the double bonds that bond the aminoalkylethoxysilane with the glutaraldehyde and the glutaraldehyde with the retainer, after bonding of the retainer.

Because of the feature such that the bridge portions are formed by reducing the double bonds that bond the aminoalkylethoxysilane with the glutaraldehyde and the glutaraldehyde with the retainer after bonding of the retainer, the reactivity of the bridge portions is reduced so that the retainer are more stably bridged to the transition metal oxide.

According to yet another feature of the invention, the transition metal oxide of the hazardous substance treatment agent has on the surface thereof hydroxyl groups intended for bonding to the bridge portions.

Providing the transition metal oxide on its surface with hydroxyl groups intended for bonding to the bridge portions enables the reliable and easy bonding of the bridge portions, which have the function of bridging the retainer to the transition metal oxide, to the transition metal oxide, increases the retaining efficiency of the retainer and also increases the treatment efficiency in inactivating the hazardous substance while inhibiting photocatalytic denaturation of the constitutive components of the treatment subject.

According to yet another feature of the invention, the transition metal oxide of the hazardous substance treatment agent is provided such that it is prevented from coming into contact with the treatment subject.

Providing the transition metal oxide so that it is prevented from coming into contact with the treatment subject enables the reliable inactivation of just the hazardous substance contained in the treatment subject without denaturing the constitutive components of the treatment subject.

According to yet another feature of the invention, the retainer of the hazardous substance treatment agent covers the transition metal oxide.

Covering the transition metal oxide with the retainer facilitates the prevention of the transition metal oxide from coming into contact with the treatment subject and enables the reliable inactivation of just the hazardous substance contained in the treatment subject without denaturing the constitutive components of the treatment subject. Furthermore, as the hazardous substance is retained in the proximity of the transition metal oxide and efficiently inactivated, the treatment efficiency in selectively inactivating a hazardous substance separated from the treatment subject is increased.

A hazardous substance treatment agent according to yet another feature of the invention has a selective retaining function to retain only a specific hazardous substance that has become mixed in or has the possibility of becoming mixed in a treatment subject that is in at least either a liquid or gaseous phase, and a photocatalytic function that inactivates the hazardous substance it retains.

By retaining only a specific hazardous substance that has become mixed in or has the possibility of becoming mixed in a treatment subject that is in at least either a liquid or gaseous phase and inactivating the retained hazardous substance by an photocatalytic action, the treatment agent is capable of efficiently inactivating a specific hazardous substance while inhibiting photocatalytic denaturation of the constitutive components of the treatment subject, thereby increasing the efficiency in treating the hazardous substance.

A hazardous substance treatment agent according to yet another feature of the invention is formed in the shape of powder or granular particles.

Forming the treatment agent in the shape of powder or granular particles offers various benefits, such that the greater surface area increases the treatment efficiency in inactivating the hazardous substance and that the range of its usage is expanded, because it can even be placed in a container having a non-standard shape, and its treatment capacity can be changed by changing, for example, the quantity of the treatment agent to be filled in the container.

According to yet another feature of the invention, the hazardous substance treatment agent is formed in a tubular shape so as to permit a treatment subject to pass through the inside of the treatment agent.

Forming the hazardous substance treatment agent in a tubular shape, inside of which a treatment subject can pass through, offers a simple structure, such as, for example, one that does not necessitate filling the treatment agent in a container but merely requires to pass the treatment subject through the interior of the treatment agent, thereby enabling the reliable treatment of a treatment subject while preventing the treatment agent from becoming mixed in the treatment subject. As a result, the treatment agent described above is capable of improving the productivity of treatment subjects that are not contaminated with hazardous substances and also offers improved medical treatment that uses such treatment subjects.

According to yet another feature of the invention, the hazardous substance treatment agent is formed in a porous shape having a plurality of communicating pores which a treatment subject can pass through.

Forming the hazardous substance treatment agent in a porous shape having a plurality of communicating pores which a treatment subject can pass through offers various benefits, such as being capable of increasing the treatment efficiency in inactivating the hazardous substance as a result of the greater surface area, facilitating formation of a structure that permits the subjects to be treated while being passed through the treatment agent, enabling the reliable treatment while preventing the base from becoming mixed in the treatment subject, improving the productivity of treatment subjects that are not contaminated with hazardous substances and offering improved medical treatment that uses such treatment subjects.

According to yet another feature of the invention, the hazardous substance is a virus, a bacterium or a toxin and has a constitutive protein that has specific binding property or antigenicity.

As a result of applying the invention to a hazardous substance which is a virus, a bacterium or a toxin and has a constitutive protein that has specific binding property or antigenicity, it is relatively easy to obtain a retainer that can easily be fixed to or included in the base having the photocatalytic ability, and it is also possible to efficiently inactivate the hazardous substance while inhibiting denaturation of the constitutive components of the treatment subject.

According to yet another feature of the invention, the transition metal oxide of the hazardous substance treatment agent is titanium oxide.

Using titanium oxide, which has a very strong photocatalytic oxidization ability, as the transition metal oxide ensures reliable inactivation of the hazardous substance.

A hazardous substance treatment device according to the present invention includes a hazardous substance treatment agent, and a light source for irradiating the transition metal oxide of said hazardous substance treatment agent with light.

By using a hazardous substance treatment agent which is capable of inactivating a hazardous substance while inhibiting denaturation of the constitutive components of the treatment subject, the hazardous substance treatment device of the invention increases the efficiency in treating the treatment subject to bring the treatment subject to the state where it is not contaminated with a hazardous substance, improves the productivity of treatment subjects that are not contaminated with hazardous substances and offers improved medical treatment that uses such treatment subjects.

A hazardous substance treatment device according to yet another feature of the invention is characterized in that the hazardous substance treatment agent is formed in the shape of powder or granular particles and that the hazardous substance treatment device includes a container which is adapted to contain said hazardous substance treatment agent and has an inflow port to introduce the treatment subject into the container and outlets that permit passage of said treatment subject while prohibiting passage of the treatment agent.

With the configuration as above, the treatment agent formed in the shape of powder or granular particles is contained in the container; the treatment subject is introduced from the inflow port into the container, in which the hazardous substance contained in the treatment subject becomes retained by the retainer of the treatment agent so that the hazardous substance is removed from the treatment subject and, meanwhile, inactivated by the photocatalytic action resulting from irradiation with the light; and the treatment subject alone is discharged through the outlets while the treatment agent is prevented from flowing through the outlets. With the feature as described above, the invention offers a simple structure which is capable of increasing the proportion of contact between the treatment subject and the retainer because of the greater surface area of the treatment agent, and treating the treatment subject while the treatment subject flows through the treatment device, thereby increasing the efficiency in treating a hazardous substance mixed in the treatment subject. Furthermore, feature described above facilitates the formation of a structure which enables the treatment without the possibility of the treatment agent remaining in the treatment subject when the treatment is completed. As such a structure permits the treatment subject to be used after treatment without a process for separating the treatment agent from the treated object, it improves the productivity of treatment subjects not contaminated with hazardous substances and offers improved medical treatment that uses such treatment subjects. As the treatment capacity can easily be changed by changing the volume of the container, the range of usage is expanded.

A hazardous substance treatment device according to yet another feature of the invention is characterized in that the light source is adapted to radiate light having a wavelength ranging from visible light to ultraviolet.

By using a light source that radiates light having a wavelength within the range of visible light to ultraviolet, in which range denaturation of the constitutive components of the treatment subject does not readily occur, the invention enables the efficient inactivation of a hazardous substance with a simple structure, thereby offering an increased treatment efficiency and easily making the treatment device compact.

A hazardous substance treatment method according to the invention calls for using a hazardous substance treatment agent that has a retainer having the specificity of retaining only a specific hazardous substance and a transition metal oxide having the photocatalytic ability to inactivate said hazardous substance retained by said retainer, bringing a treatment subject, which is in at least either a liquid or gaseous phase and in which said hazardous substance is either contained or presents the possibility of becoming mixed, into contact with said treatment agent, and irradiating said transition metal oxide with light.

By causing the retainer to retain only a specific hazardous substance that has become mixed in or has the possibility of becoming mixed in the treatment subject that is in at least either a liquid or gaseous phase and inactivating said hazardous substance retained by the retainer by means of a photocatalytic action of the transition metal oxide irradiated with light, the present invention is capable of efficiently inactivating a specific hazardous substance while inhibiting photocatalytic denaturation of the constitutive components of the treatment subject, thereby increasing the efficiency in treating the hazardous substance.

A hazardous substance treatment method according to yet another feature of the invention calls for irradiating the hazardous substance treatment agent with light after the treatment subject is in contact with said hazardous substance treatment agent for a given period of time.

By keeping the treatment subject in contact with the treatment agent for a given period of time so that a hazardous substance is retained by the treatment agent, and then irradiating the hazardous substance treatment agent with light under the condition that the treatment agent is not in contact with the treatment agent, the invention enables the reliable and exclusive inactivation of the hazardous substance without denaturation of the constitutive components of the treatment subject.

BRIEF DESCRIPTION OF THE DRAWINGS

FIG. 7 is a schematic illustration to explain how the subject of treatment is treated in the main body of a treatment device according to another embodiment of the invention; FIG. 8 is a schematic illustration to explain how the subject of treatment is treated in the main body of a treatment device according to yet another embodiment of the invention.

PREFERRED EMBODIMENT OF THE INVENTION

Next, the structure of a hazardous substance treatment device according to an embodiment of the present invention is explained hereunder, referring to the relevant drawings.

Figure 2:
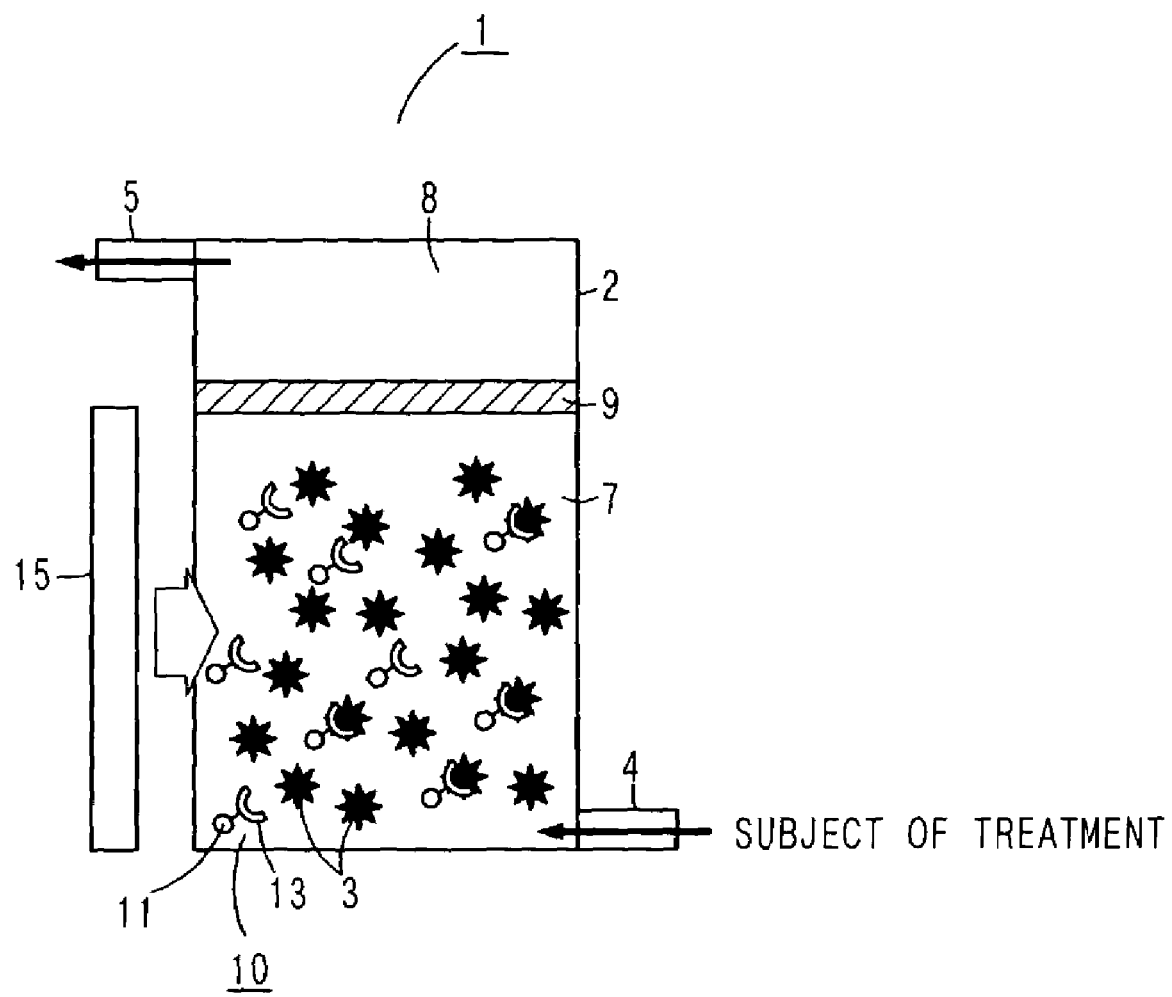
FIG. 2 is a schematic illustration to explain how the subject of treatment is treated in the main body of a treatment device according to said embodiment of the invention.

Referring to FIG. 2, numeral 1 denotes a treatment device body. The treatment device body 1 has a container 2, which is formed of a translucent material, such as glass, in a cylindrical shape. An inflow port (not shown) is open at the bottom of the container 2. The inflow port communicates with an inflow canal 4 for introducing the subject of treatment, which is in at least either a liquid or gaseous phase. The treatment subject to be introduced through the inflow canal 4 is a substance that either contains or presents the danger of entry of a hazardous substance 3, examples of which include various viruses, bacteria and toxins. The hazardous substance 3 characteristically has a constitutive protein that has specific binding property or antigenicity. As shown in Table 1, there are principally three locations where the body of a germ shows strong antigenicity, with different bacteria showing different types of antigenicity.

For example, *E-coli* O-157, which is a bacterium, has No. 157 O-antigen. The treatment device functions to treat any of a number of bacteria that show such a specific antigenicity. Among viruses, any virus having a constitutive protein that either has a strong antigenicity or shows the strong binding effect with its receptor is among the objects of inactivation. The examples of such viruses are shown in Table 2. As for toxins, a number of toxins that show specific antigenicity, including swellfish poison (tetrodotoxin), snake poison and various toxins of insects, such as scorpions, wasps, spiders, etc., are included in the objects of inactivation, in addition to various toxins produced by bacteria, examples of which are shown in Table 3.

TABLE 1

[Bacteria]

| Antigen | Location | Antibody |
|---|---|---|
| O-antigen | envelope | O-antibody |
| K-antigen | capsule | K-antibody |
| H-antigen | flagellum | H-antibody |

Table 2

[See Attached Sheet]

Table 3

[See Attached Sheet]

An outflow canal 5 to discharge the treatment subject out of the container 2 is provided at the upper part of the container 2. A return canal (not shown) adapted to permit a part of the discharged treatment subject to return through the inflow canal 4 into the container 2 branches off from the outflow canal 5. Thus, the treatment device has a structure that circulates a part of the treatment subject.

A filter 9 is disposed in the upper part of the container 2 so that the filter 9 divides the interior of the container 9 into two sections: a treatment chamber 7 which is located underneath the filter 9 and communicates with the inflow canal 4, and an outflow chamber 8 which is located above the filter 9 and communicates with the outflow canal 5. The treatment chamber 7 is filled with a treatment agent 10 in the form of powder or granular particles. A plurality of outlets which permit the treatment subject to pass therethrough while prohibiting passage of the treatment agent 10 are open in the filter 9.

As shown in FIGS. 1 and 2, the treatment agent 10 is comprised of a base 11, bridging molecules 12 serving as bridge portions, and a retainer 13 having specificity such that it may bind only with a specific hazardous substance 3. The retainer 13 bonds through the bridging molecules 12 to the surface of the base 11 formed of powdery or granular titanium oxide, which is a transition metal oxide. To be more specific, the retainer 13 bonds to the base 11 in such a manner that 3-aminopropyl-triethoxysilane, for example, which is an aminoalkylethoxysilane, is bonded to hydroxyl groups to be bonded to the surface of the titanium oxide; glutaraldehyde is bonded to the amino groups of the 3-aminopropyl-triethoxysilane; the amino groups of the retainer 13, which is a protein, are bonded to the aldehyde groups at the ends of the glutaraldehyde molecules; and that the Schiff bases are reduced, in other words the double bonds that bond the aminoalkylethoxysilane with the glutaraldehyde and the glutaraldehyde with the retainer 13 are reduced after bonding the retainer 13. The substance used as the retainer 13 has to have the characteristic property of specifically retaining the hazardous substance 3. In other words, substances that include amino groups having the specificity of being capable of bonding only to the hazardous substance 3 or proteins having such specificity can be used. Examples of such substances and proteins include specific antibodies against specific antigenicities of bacteria listed in Table 1, receptors which are listed in Table 2 and function to receive the constitutive proteins of viruses having strong and specific bonding ability, specific antibodies against specific virus antigens, and antibodies against toxins listed in Table 3.

The treatment agent 10 is filled in the treatment chamber 7 with its concentration to the treatment subject introduced into the chamber desirably ranging from 0.0625 to 1 wt %, more desirably from 0.125 to 0.5 wt %, or even more desirably at 0.25 wt %. Should the mass concentration of the treatment agent 10 be less than 0.0625 wt % or exceed 1 wt %, an increased amount of the hazardous substance 3 would remain untreated. Therefore, the concentration of the treatment agent 10 is set in the range from 0.0625 to 1 wt %, more desirably from 0.125 to 0.5 wt %, or even more desirably at 0.25 wt %.

The treatment device body 1 is provided with a light source for irradiating the treatment agent 10 in the treatment chamber 7. Examples of lamps that can be used as the light source 15 include fluorescent lamps that emit visible light having a peak wavelength of approximately 600 nm, black lights having a peak wavelength ranging 300 nm to 420 nm, and ultraviolet lamps, such as low pressure mercury lamps having the ability of generating ozone even at an approximately 185 nm, which is its peak wavelength. Long-wave light ranging from visible light to light that having a wavelength longer than infrared is not capable of energizing transition metal oxide and, therefore, does not have the photocatalytic ability. Light having too short a wavelength, however, is prone to damaging the constitutive components of the treatment subject or the treatment agent 10. Therefore, the light source 15 used for the embodiment has a peak wavelength ranging from approximately 150 nm to approximately 600 nm, which is the range covered by the visible light and ultraviolet.

The process of producing the treatment agent of the embodiment described above is explained hereunder, referring to the relevant drawings.

First, as shown in FIG. 3(*a*), a base 11 prepared by using powder or granular particles of titanium oxide and bonding hydroxyl groups to the titanium oxide on the surface of each particle by any appropriate means, such as washing with nitric acid or the like and drying thereafter. The base 11 thus prepared is mixed with toluene containing an aminoalkylethoxysilane, i.e. 3-aminopropyl-triethoxysilane, and the mixture is circulated. As a result of the circulation, the 3-aminopropyl-triethoxysilane bonds to the surface of the base 11, with the ethoxy groups of the 3-aminopropyl-triethoxysilane bonding to the hydroxyl groups of the base 11 as shown in FIG. 3(*b*). Upon completion of the reaction as a result of the circulation for a given period of time, the base 11 is washed with alcohol, such as methanol, and a potassium phosphate buffer solution. Thereafter, the base 11, which is in the state that 3-aminopropyl-triethoxysilane is bonded to the titanium oxide located on the surface of the base 11, is dispersed into the potassium phosphate buffer solution. Thus, a first suspension is prepared.

Next, an aqueous solution of glutaraldehyde is stirred into the prepared suspension so that the glutaraldehyde bonds to the amino groups of the 3-aminopropyl-triethoxysilane as shown in FIG. 3(*c*). Then, the mixture is washed with a potassium phosphate buffer solution, and the base 11, on the surface of which bridging molecules 12 have been formed by bonding the glutaraldehyde as described above, is dispersed into the potassium phosphate buffer solution. Thus, a second suspension is prepared.

Figure 3:
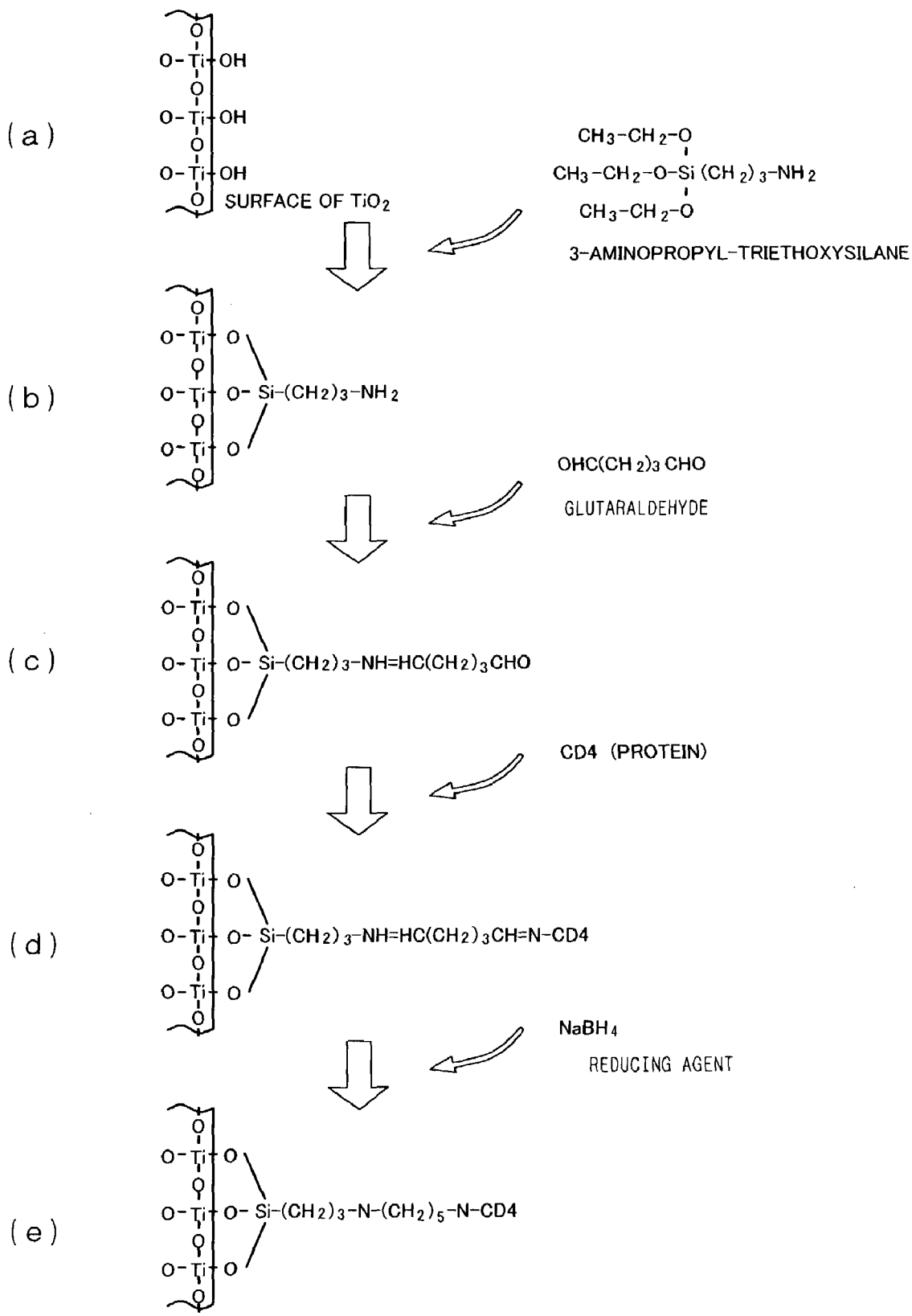
FIG. 3 is a flow chart showing the process of holding a retainer onto a base of said device.

Thereafter, a solution containing the retainer 13, which is a protein, is stirred into the second suspension. In case of the present embodiment, the retainer 13 is CD4 ([Cys(Bzl)]$^{84}$-Fragment 81-92: a product of Sigma-Aldrich). CD4 is a constitutive protein on the surface of the T cell, and a receptor that combines with HIV (Human Immunodeficiency Virus). As shown in FIG. 3(d), the amino groups of CD4, which serves as the retainer 13, bond to the aldehyde groups of the bridging molecules 12 so that the retainer 13, i.e. CD4, are fixed to the base 11. Then, a third suspension is prepared by separating and collecting the base 11 retaining the retainer 13 (CD4) by filtration, washing the collected base 11 with an aqueous solution of sodium chloride, and dispersing the base 11 into a buffer solution of diluted hydrochloric acid so as to inactivate the aldehyde groups.

Figure 1:
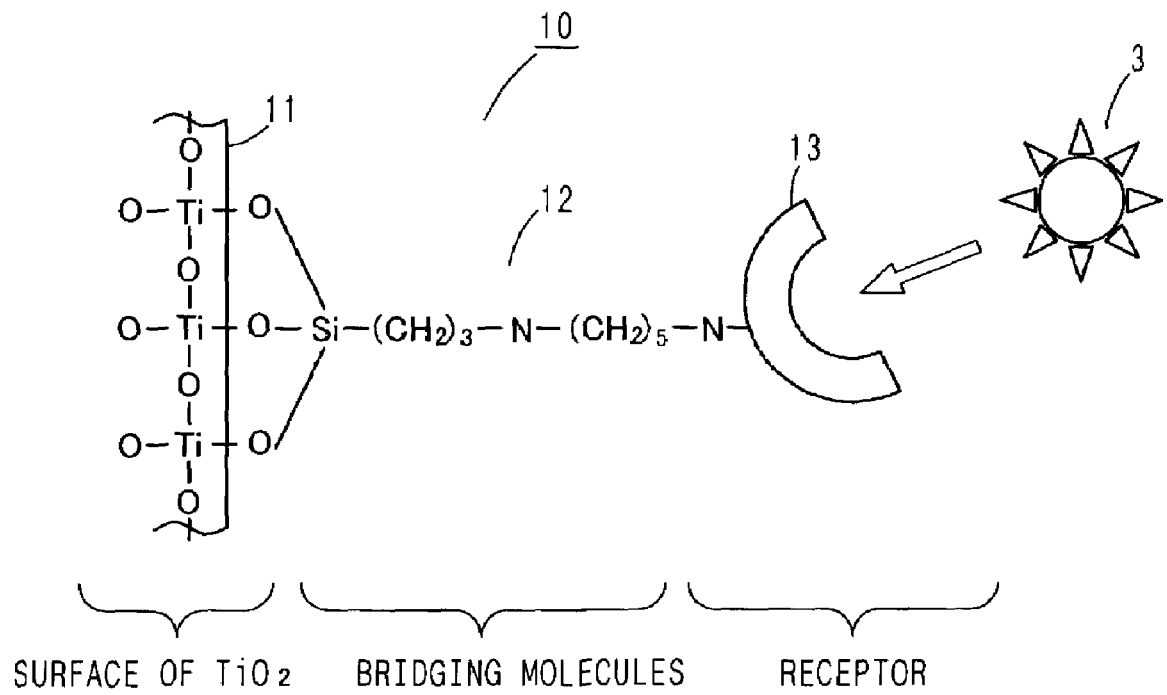
FIG. 1 is a schematic illustration to explain how a hazardous substance treatment agent according to an embodiment of the present invention selectively retains a hazardous substance.

Sodium boron hydride is added to the third suspension so as to reduce the Schiff bases, in other words reduce the double bonds that bond the aminoalkylethoxysilane with the glutaraldehyde and the glutaraldehyde with CD4, which serves as the retainer 13. Thus, the treatment agent 10 shown in FIG. 1 and FIG. 3(e) is prepared.

Next, the process of treating a treatment subject according to the embodiment described above is explained hereunder.

First, a treatment agent 10 containing the retainer 13 to retain the specific antigenicity of the hazardous substance 3, which is the substance to be removed from the treatment subject, is prepared as described above and filled in the treatment chamber 7. The treatment subject is a liquid, such as blood, a blood component or a blood derivative, or a gas, such as the air.

The treatment subject is introduced at a given flow rate through the inflow canal 4 of the treatment device body 1 into the treatment chamber 7, which is filled with the treatment agent, while the treatment subject is irradiated with the light emitted by the light source 15.

As a result of the introduction of the treatment subject, the hazardous substance 3 in the treatment subject is adsorbed by or otherwise combined with the retainer 13 of the treatment agent 13. While the hazardous substance 3 is thus inactivated, the treatment subject flows through the filter 9 into the outflow chamber 8 and flows out of the outflow chamber 8 through the outflow canal 5. Thus, the hazardous substance 3 is removed from the treatment subject. The hazardous substance 3 retained and inactivated by the retainer 13 is decomposed by the strong oxidizing ability of the titanium oxide, which functions as a photocatalyst because of the light emitted by the light source 15. The photocatalytic action progresses such that oxidation reaction, i.e. generation of hydroxyl radicals (—OH), is caused by collision of the moisture ($H_2O$) in the air or the moisture on the surface of the titanium oxide irradiated with the light from the light source 15 against the surface of the titanium oxide, while reduction, i.e. generation of superoxide anions (—$O_2$), is caused by collision of the oxygen. The photocatalytic action purifies the treatment subject, thereby reliably preventing the hazardous substance 3 from causing diseases or the like.

Next, the function of the treatment agent according to the embodiment described above is explained, referring to the actual examples.

ACTUAL EXAMPLE 1

A test was performed to evaluate the anti-HIV capability of the treatment agent 10, which is intended to inactivate HIV (the hazardous substance) and to which CD4 serving as the retainer 13 was bonded.

The treatment subject used in the test was prepared so that the concentration of P24 antigen of HIV in 500 µl of RPMI culture medium was 100 ng/ml.

As for preparation of the treatment agent 10, titanium oxide powder (a product of WAKO PURE CHEMICAL INDUSTRIES: special grade chemical) was added to a toluene solution that had been prepared beforehand by mixing 3-aminopropyl-triethoxysilane (a product of TOKYO KASEI KOGYO CO., LTD.: reagent) at a given concentration into toluene (a product of WAKO PURE CHEMICAL INDUSTRIES: reagent), and, after being circulated for a given period time, the mixture was washed with ethanol and a 0.1 M potassium phosphate buffer solution (pH 7.5), which had been prepared beforehand, and then dispersed in a given quantity of the 0.1 M potassium phosphate buffer solution. Thus, a first suspension was prepared. An aqueous solution of glutaraldehyde (a product of TOKYO KASEI KOGYO CO., LTD.: reagent), which had been prepared at a given concentration beforehand, was added to the first suspension and stirred at room temperature until mixed. Thereafter, the mixture was washed again with the 0.1 M potassium phosphate buffer solution and dispersed in a given quantity of the 0.1 M potassium phosphate buffer solution, thereby preparing a second suspension. Then, a solution containing CD4([Cys(Bzl)]$^{84}$-Fragment 81-92: a product of Sigma-Aldrich) was stirred and mixed into the second suspension, and the mixture was stirred for 24 hours at 4° C. After dehydration by solid-liquid separation, a third suspension was prepared by suspending the dehydrated components in a 1 M Tris-HCL buffer solution (pH 7.5) and allowing a reaction to progress for one hour at room temperature in this state. Thereafter, sodium boron hydride was added to the third suspension, and a reaction was allowed to progress for thirty minutes at room temperature. After being washed with the 0.1 M potassium phosphate buffer solution, the resulting components were dispersed in a given quantity of the 0.1 M potassium phosphate buffer solution. Thus, a treatment agent buffer solution comprising the potassium phosphate buffer solution and the buffer suspended in the potassium phosphate buffer solution was prepared. The treatment agent buffer solution prepared as above was stored at 4° C.

Figure 4:
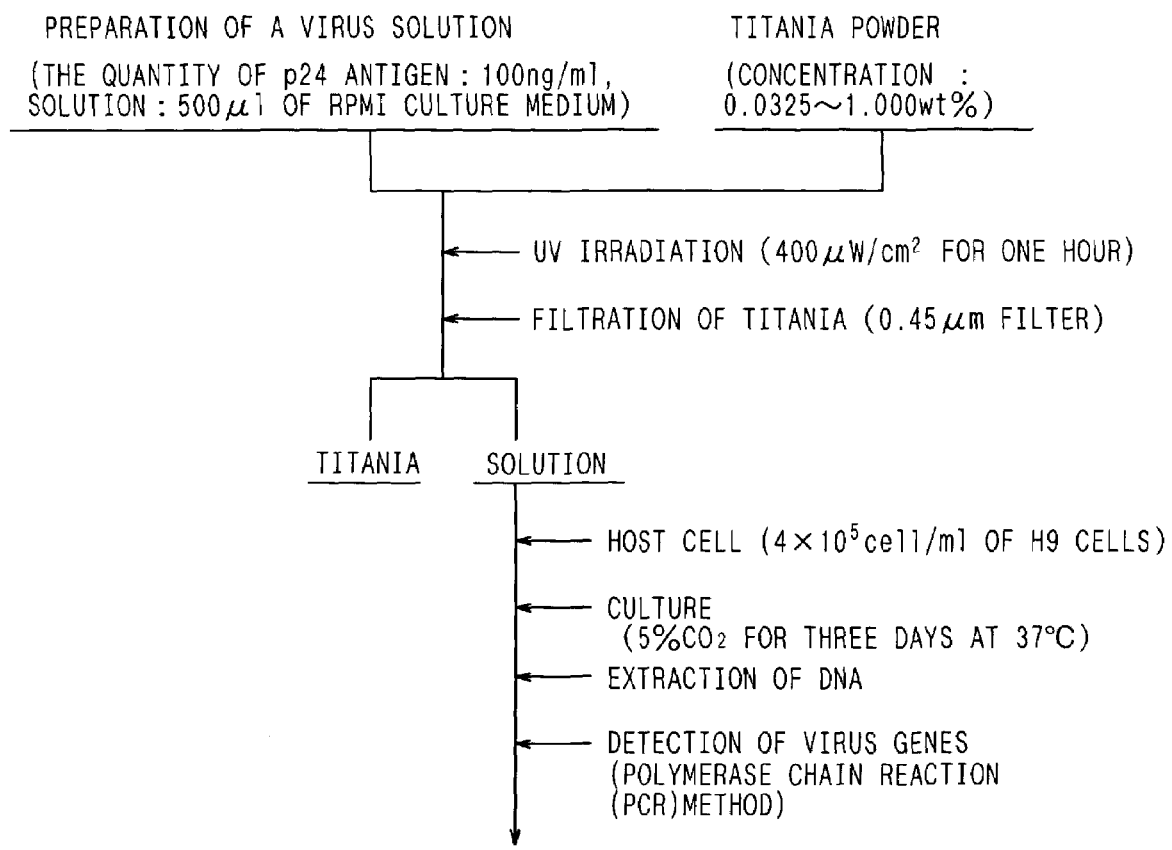
FIG. 4 is a flow chart of a test to confirm the concentration of said hazardous substance treatment agent.

The test for confirming the anti-HIV function of the treatment agent was performed as shown in FIG. 4. First, the treatment agent buffer solution was mixed with the treatment subject prepared as above so that the concentration of the treatment agent was at a given level. Then, after the mixture was irradiated with 400 µW/cm$^2$ of ultraviolet for one hour by using a 10W black light serving as the light source 15, the treatment agent was passed through a 0.45 µm filter. Thereafter, H9 cells (CD4-positive T cells), which are host cells to HIV, were mixed with the solution that had been separated through the filtration and consisted of the treatment agent and the culture medium solution with a mixing ratio of 4×10$^5$ cells/ml and cultured for three days under the conditions of 37° C. and 5% $CO_2$. After the culture, DNA was extracted from the H9 cells, and the virus genes were amplified through PCR (polymerase chain reaction). By evaluating the amplified genes after the treatment, the survival rate of infectious viruses was quantified, with its results shown in Table 4.

TABLE 4

| TiO2 Concentration [wt %] | HIV Inactivating Ratio [%] |
|---|---|
| 1 | 88 ± 8 |
| 0.5 | 94 ± 4 |
| 0.25 | 100 |
| 0.125 | 92 ± 5 |
| 0.0625 | 85 ± 15 |
| 0 | 0 |

As it is evident from the test results shown in Table 4, the treatment agent 10 exhibited the germicidal effect when its concentration was in the range from 0.0625 to 1 wt %, more desirably from 0.125 to 0.5 wt %, or even more desirably at 0.25 wt %.

ACTUAL EXAMPLE 2

Next, a test was performed to evaluate the treatment efficiency in treating a hazardous substance 3 by giving titanium oxide having the photocatalytic ability the specificity that would permit combining with the hazardous substance 3.

The solution identical to the treatment agent buffer solution used in Actual Example 1 described above was used as the treatment agent 10. The treatment subject used in this test was prepared so that the concentration of P24 antigen of HIV in 500 μl of human blood serum was 100 ng/ml.

Figure 5:
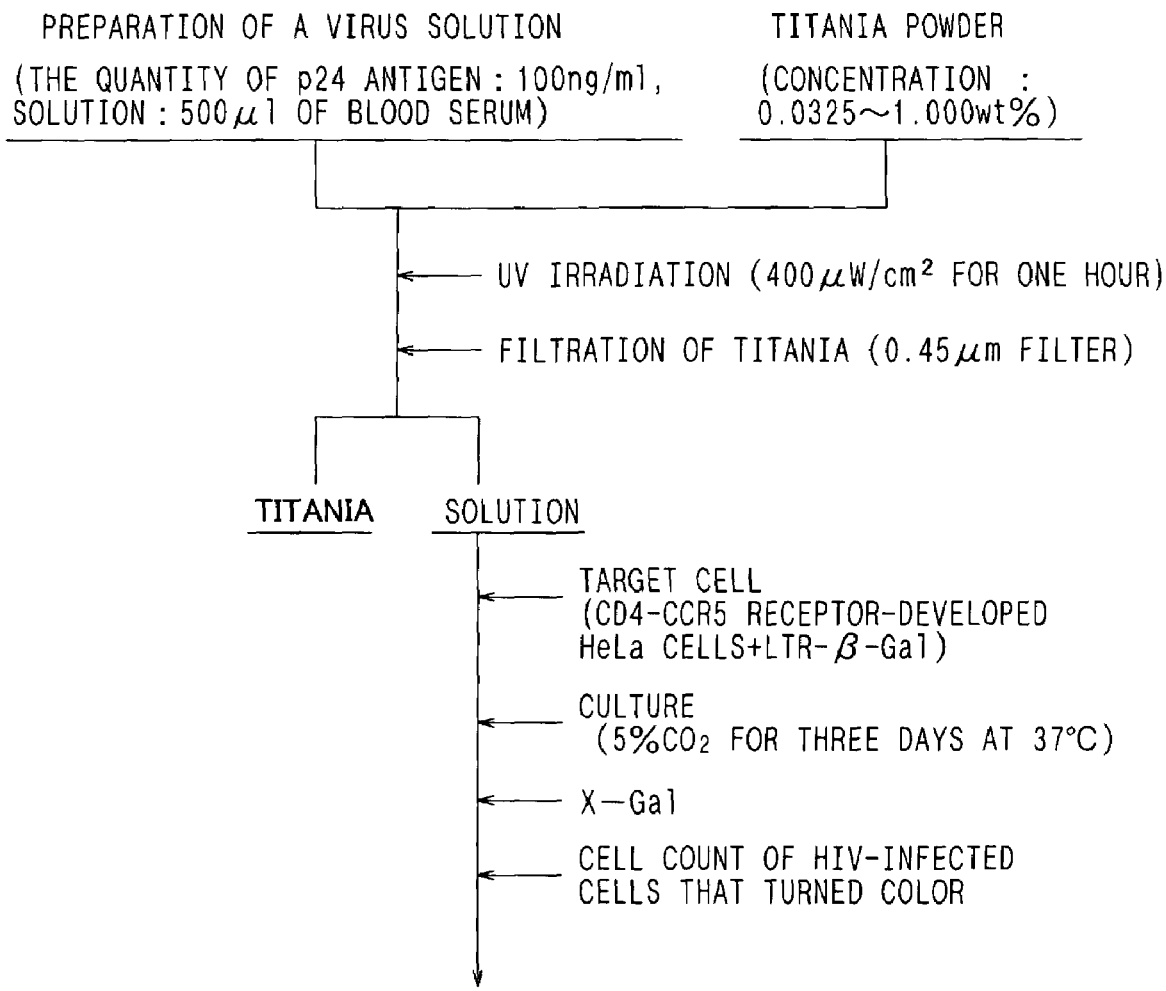
FIG. 5 is a flow chart of a test to verify whether that the hazardous substance has been inactivated by said hazardous substance treatment agent.

The test for confirming the treatment efficiency was performed as shown in FIG. 5. First, the treatment agent buffer solution was added to the treatment subject prepared as above so that the concentration of the treatment agent was 0.25 wt %. Then, after the mixture was irradiated with 400 μW/cm² of ultraviolet for one hour by using a 10W black light serving as the light source 15, the treatment agent 10 was passed through a 0.45 μm filter. Thereafter, by using the solution that had thus been separated, HeLa cells having HIV-infected receptors, i.e. CD4 and CCR5, developed therein were cultured under the conditions of 5% $CO_2$ for three days. As the HeLa cells have a mechanism of causing â-gal to be induced by an HIV promoter, infection with HIV produces â-gal in the cells so that the cells become blue when X-gal is added after culture. Therefore, by counting the number of cells that had turned blue, the degree of infection with the virus was indirectly determined.

Figure 6:
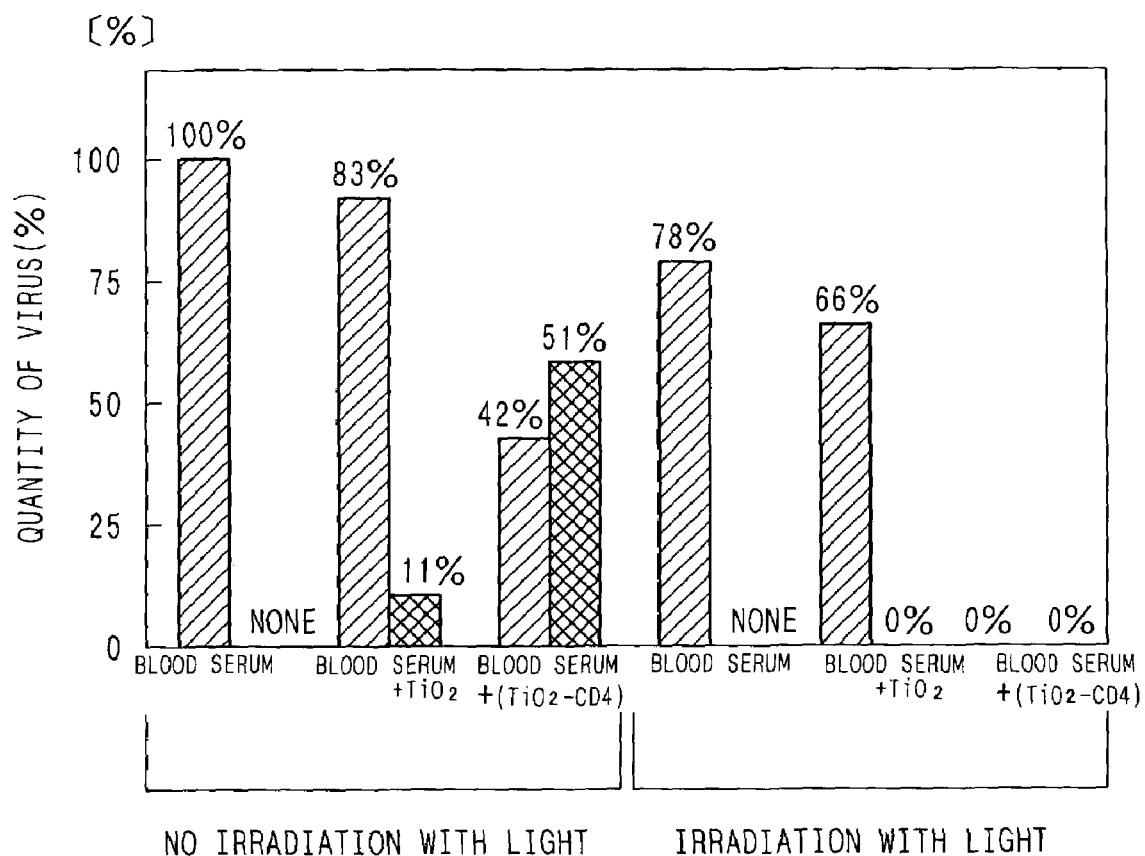
FIG. 6 is a graph showing results of said test to confirm inactivation of the hazardous substance by the hazardous substance treatment agent.

As a comparison example, a test was performed to evaluate the treatment efficiency in the same manner as Actual Example 2 described above, except that an titanium oxide buffer solution that had been prepared without binding CD4 was used in the place of the treatment agent buffer solution used in Actual Example 2. Furthermore, a comparative evaluation was performed also regarding the anti-HIV action caused by irradiation with ultraviolet, with its results shown in FIG. 6. In FIG. 6, the samples to which neither treatment agent buffer solution nor titanium oxide buffer solution was added are referred to as blood serum, while the samples containing the titanium oxide buffer solution and the samples containing the treatment agent buffer solution are referred to as blood serum+$TiO_2$ and blood serum+$TiO_2$–CD4 respectively.

With regard to the samples containing neither treatment agent buffer solution nor titanium oxide buffer solution, the test results shown in FIG. 6 exhibited slight reduction in the quantity of infectious HIV in the blood serum resulting from ultraviolet irradiation, but no significant inactivation of HIV was seen.

Under the condition that ultraviolet irradiation was not performed, each sample with the titanium oxide buffer solution or the treatment agent buffer solution added exhibited that a part of the HIV in the blood serum was attached to titanium oxide particles. The samples combined with CD4 showed a greater quantity of HIV attached. In other words, as the difference between the amount of HIV retained by the titanium oxide to which CD4 was bonded and the amount of HIV attaching to the titanium oxide particles is the quantity of HIV selectively attaching to CD4, the test proved that bonding CD4 to titanium oxide enables the treatment agent 10 to selectively retain HIV.

Under the condition that ultraviolet irradiation was performed, each sample with the titanium oxide buffer solution added showed reduction in the quantity of infectious HIV in the solution that had been separated from the solid substance, while no infectious HIV was seen on the surface of the solid, i.e. the titanium oxide particles. In the samples containing the treatment agent buffer solution, no infectious HIV was seen in either the solution or the solid. The treatment agent thus proved to have the ability of completely killing or inactivating the HIV in the solution.

Merely using the photocatalytic function of the titanium oxide presents the possibility of the photocatalytic oxidization not only killing or otherwise inactivating HIV but also acting on the constitutive proteins that constitute the blood serum. As the photocatalytic oxidization ability of the titanium oxide is thus inhibited from effectively acting just for inactivation of HIV, resulting in such problems as incomplete elimination of infectious HIV and denaturation of components of the blood serum. Therefore, a method that calls for adding titanium oxide alone to the treatment subject requires ultraviolet irradiation for a long period of time so as to exert the strong photocatalytic oxidizing action for an extended period to completely inactivate HIV. It is evident from the above test results that prolonged photocatalytic action increases the proportion of denatured components in the blood serum, thereby diminishing or impairing the normal function of the blood serum. However, the test results show that causing titanium oxide to retain CD4, which has the function of selectively adsorbing HIV, enables the photocatalytic oxidization ability of the titanium oxide to effectively promote inactivation of HIV, thereby inhibiting denaturation of constitutive components of blood serum to an absolute minimum and ensuring the primary function of the blood serum.

As is seen from the foregoing, providing the base 11, which is comprised of titanium oxide or other substance that has the photocatalytic ability, with a retainer 13 for retaining only a specific hazardous substance 3, such as HIV, ensures the reliable and efficient inactivation of the hazardous substance 3 while inhibiting denaturation of components of the treatment subject, such as blood serum.

ACTUAL EXAMPLE 3

Next, a test was performed to evaluate the treatment efficiency in treating a hazardous substance 3 by giving titanium oxide having the photocatalytic ability the specificity that would permit combining with the hazardous substance 3.

To be more specific, the test was performed to determine the treatment efficiency in sterilization of blood that had been drawn for a clinical examination.

The hazardous substance treatment device used for the test had a container serving as the base. The container had a width of 10 mm, a depth of 10 mm and a thickness of 30 mm and was formed of quartz glass that allowed the passage of nearly 100% of visible light and ultraviolet having a wavelength of not less than 300 nm. A film of titanium oxide having a thickness of approximately 1 ìm was formed on the inner surface of the container by a conventional sol-gel method. The titanium oxide film was confirmed to have the ability of absorbing approximately 90% of ultraviolet having a wavelength around 380 nm. It is probable that approximately 90% of ultraviolet was converted to the oxidization-reduction ability of the photocatalytic action.

As is mentioned above, the container itself served as the treatment agent, with CD4 serving as the retainer 13 fixed to the titanium oxide film in the same manner as Actual Example 1.

A black light having a peak wavelength of 360 nm (a product of Toshiba Lighting & Technology Corporation) served as the light source 15 and was set such that its radiation intensity was 500 µW/cm$^2$ by using a luminance meter (UM-10; the light receptance unit: UN-360; a product of Minolta Co., Ltd.)

The treatment subject used in this test was a blood serum component separated from human blood and prepared so that the concentration of P24 antigen of HIV was 500 ng/ml.

The treatment efficiency was evaluated based on the function of inhibiting HIV infection, which is virion destruction function.

To be more precise, blood serum containing HIV was injected into the container. The container was then set in a shaking incubator and irradiated with ultraviolet from the black light while being shaken lightly. The period of ultraviolet irradiation was set for various appropriate lengths of time ranging from 10 to 60 minutes. After the ultraviolet irradiation, 500 ìl of serum was taken from the container. The serum sample was cultured under the conditions of 37° C. and 5% $CO_2$ for two hours together with HeLa cells from which CD4 had developed, so that the serum was infected. After the culture, the serum was removed, and the HeLa cells were further cultured in a cell culture solution under the same conditions as above for three days. Then, in the same manner as in case of Actual Example 2, the degree of infection with the virus was indirectly determined by counting the number of cells that had turned blue due to reaction with â-gal produced in the cells as a result of the infection. Thus, the function of inhibiting HIV infection was evaluated.

As a blank test, blood containing HIV was injected into the container, which was then set and left in a shaking incubator without ultraviolet irradiated. After being shaken lightly, the sample was taken from the container and cultured together with HeLa cells, from which CD4 had developed, in the same manner as Actual Example 3 described above to determine the quantity of virus infection, with its results shown in Table 5.

TABLE 5

| $TiO_2 + CD_4$ | UV | Period of UV Irradiation (min.) | | | | | | |
|---|---|---|---|---|---|---|---|---|
| | | 0 | 10 | 20 | 30 | 40 | 50 | 60 |
| + | + | 420 | 280 | 110 | 0 | 0 | 0 | 0 |
| + | − | 410 | 360 | 350 | 340 | 340 | 340 | 330 |
| − | + | 420 | 350 | 320 | 310 | 300 | 290 | 270 |
| − | − | 420 | 410 | 410 | 410 | 400 | 400 | 400 |

Number of Infected Cells ( /well)

NB) +: present
−: absent

As is evident from the above results shown in Table 5, reduction in the number of infectious viruses was seen even in the blank samples that had not received ultraviolet irradiation. It can be surmised that the number of infectious viruses was reduced due to adsorption of HIV by the adsorption ability of CD4 fixed to the surface of the titanium oxide on the inner surface of the container. The longer the period of ultraviolet irradiation, the smaller the amount of infectious viruses; after irradiation for 30 minutes or more, no infectious virus was recognized. In other words, it was proved that ultraviolet irradiation for not less than 30 minutes resulted in inactivation of HIV by the photocatalytic action, thereby preventing HIV infection. Therefore, if used for, for example, sterilization of blood serum for the purpose of a clinical examination of drawn blood, the treatment agent is capable of specific sterilization of a given hazardous substance 3 while inhibiting denaturation of constitutive components of the blood serum. In other words, the range of usage of the invention includes sterilization performed as preliminary treatment of blood intended for a clinical examination, which was heretofore impossible to be sterilized prior to the clinical examination.

ACTUAL EXAMPLE 4

Next, a test was performed to evaluate the treatment efficiency of treating a hazardous substance 3 in the same manner as Actual Example 3 described above.

A container formed of quartz glass and having a width of 10 mm, a depth of 10 mm and a thickness of 30 mm was used as the treatment device for treating a hazardous substance. In the same manner as in the case of Actual Example 3, a film of titanium oxide was formed on the surface of glass beads having a diameter of 0.5 mm by a conventional sol-gel method. Then, CD4 was fixed to the surface of the titanium oxide film of the glass beads in the same manner as in the case of Actual Example 1. The glass beads having CD4 fixed thereto were filled in the container, and a black light was set in the same manner as in the case of Actual Example 3 so that its irradiation luminance was 500 µW/cm$^2$. Thus, the treatment device was form.

In the same manner as in the case of Actual Example 3, blood containing HIV was injected into the container and irradiated with ultraviolet. Thereafter, the blood underwent culture with HeLa cells from which CD4 had developed, and the degree of infection with the virus was determined, with its results shown in Table 6.

TABLE 6

| $TiO_2 + CD_4$ | UV | Period of UV Irradiation (min.) | | | | | | |
|---|---|---|---|---|---|---|---|---|
| | | 0 | 10 | 20 | 30 | 40 | 50 | 60 |
| + | + | 370 | 210 | 40 | 0 | 0 | 0 | 0 |
| + | − | 390 | 310 | 310 | 300 | 300 | 300 | 300 |
| − | + | 480 | 340 | 320 | 300 | 290 | 290 | 270 |

TABLE 6-continued

| TiO$_2$ + CD$_4$ | UV | Period of UV Irradiation (min.) | | | | | | |
|---|---|---|---|---|---|---|---|---|
| | | 0 | 10 | 20 | 30 | 40 | 50 | 60 |
| – | – | 400 | 390 | 390 | 390 | 390 | 390 | 390 |
| | | Number of Infected Cells ( /well) | | | | | | |

NB) +: present
−: absent

As is true in Actual Example 3, the above results in Table 6, too, show reduction in the number of infectious viruses even in the blank samples that had not received ultraviolet irradiation. Like Actual Example 3, it can be surmised that the number of infectious viruses was reduced due to adsorption of HIV by the adsorption ability of CD4 fixed to the surface of the titanium oxide. The longer the period of ultraviolet irradiation, the smaller the amount of infectious viruses; after irradiation for 30 minutes or more, no infectious virus was recognized. In other words, as is true in Actual Example 3, it was proved that ultraviolet irradiation for not less than 30 minutes resulted in inactivation of HIV by the photocatalytic action, thereby preventing HIV infection.

In the case of Actual Example 4, the amount of infectious viruses in the blank samples, which had not been exposed to ultraviolet radiation, and the amount of infectious viruses that had survived ultraviolet irradiation were both smaller than those of Actual Example 3 respectively. It seems that the surface area of the titanium oxide film on the glass beads of Actual Example 4, which is greater than the surface area of the titanium oxide film on the inner surface of the container of Actual Example 3, resulted in adsorption of a greater amount of HIV and a greater photocatalytic ability of titanium oxide than in the case of Actual Example 3, ultimately leading to more efficient treatment. Therefore, if used for, for example, preliminary treatment for a clinical examination, the invention is capable of reduction of the duration of sterilization, thereby reducing the period required to obtain results of the clinical examination and enabling the efficient treatment of blood for the clinical examination.

As described above, according to the present embodiment, a retainer 13, which is a protein having amino groups and has the specificity of being capable of bonding only to a particular hazardous substance 3, is provided and held onto the surface of the base 11 comprised of titanium oxide having the photocatalytic ability. The retainer 13 is held onto the surface of the base 11 by bridging molecules 12 which have aldehyde groups at the ends, with said amino groups of the retainer 13 bonding to the aldehyde groups of the bridging molecules 12. Because of this feature, the ability of adsorbing a specific hazardous substance as well as the photocatalytic ability can easily be obtained. By bringing a treatment subject containing a hazardous substance 3 into contact with the retainer 13, thereby removing the hazardous substance 3 from the treatment subject and bonding it to the retainer 13, the embodiment enables the reliable inactivation of the hazardous substance 3 by photocatalytic action. As this feature prevents undesirable decomposition of constitutive components of the treatment subject by the photocatalytic action, the embodiment enables the efficient inactivation of a specific hazardous substance 3 contained in the treatment subject and thus increases the efficiency of treating the hazardous substance 3 in the treatment subject without the danger of impairing the function of the treatment subject.

The bridging molecules 12 for holding the retainer 13 onto the surface of the base 11, which is provided, on at least its surface, with a transition metal oxide having the photocatalytic ability, such as titanium oxide, is formed by bonding an aminoalkylethoxysilane to said transition metal oxide and bonding glutaraldehyde to amino groups at the ends of the aminoalkylethoxysilane so that the bridging molecules 12 are provided, at the ends thereof, with aldehyde groups intended for bonding to amino groups of the retainer 13. As the base 11 having the photocatalytic ability is ensured of being provided with a retainer 13 that has the specificity of being capable of bonding only to a particular hazardous substance 3, the ability of adsorbing a specific hazardous substance as well as the photocatalytic ability can easily be obtained to efficiently inactivate the hazardous substance 3 without impairing the function of the treatment subject.

Another feature of the embodiment lies in that the bridging molecules 12 are formed by reducing the double bonds that bond the aminoalkylethoxysilane with the glutaraldehyde and the glutaraldehyde with the retainer 13, after bonding of the retainer 13. Because of this feature, the reactivity of the bridging molecules 12 is reduced so that the retainer 13 can be held onto the base 11 more stably. As a result, the efficiency of treating a hazardous substance 3 is increased, while denaturation of components of the treatment subject is more effectively inhibited.

The transition metal oxide used in the embodiment described above is titanium oxide that has strong photocatalytic oxidizing ability and permits hydroxyl groups, which are intended for formation of bridging molecules 12, to bond to its surface at room temperature in the presence of the air. As a result of this feature, the embodiment is capable of increasing the boding efficiency of the retainer 13 and the efficiency of treating a hazardous substance 3, and more effectively inhibiting denaturation of components of the treatment subject.

According to the embodiment, a treatment agent 10 comprised of a base 11, which is titanium oxide in the state of powder or granular particles, bridging molecules 12 and a retainer 13 held onto the base 11 via the bridging molecules 12 is contained in a treatment chamber 7 of a container 2 having an inflow port and outlets, said outlets prohibiting passage of the treatment agent 10; a treatment subject is introduced through an inflow canal 4 into the treatment chamber 7, in which the retainer 13 of the treatment agent 10 catches and retains a hazardous substance 3 mixed in the treatment subject so that the hazardous substance 3 is removed from the treatment subject and inactivated by the photocatalytic action; and the treatment subject alone is discharged from an outflow canal 5 while the treatment agent remains in the treatment chamber 7. The powdery or granular shape of the base 11, which functions to hold the retainer 13, gives the base 11 a great surface area and increases the retaining capacity of the retainer 13 and the proportion of contact with the treatment subject, thereby enabling the more effective inactivation of the hazardous substance 3 and, consequently, the more effective suppression of denaturation of constitutive components of the treatment subject. As the treatment subject can be used after treatment without the need of a process for separating the treatment agent 10 from the treated object, the embodiment offers an increased treatment efficiency by not only facilitating the process of treating a treatment subject but also enabling the continuous feeding and treatment of the treatment subject. Because the treatment capacity can easily be changed by changing the volume of the treatment chamber 7 of the container so as to change the amount of the treatment agent to be filled in the treatment chamber 7, the embodiment offers a wide range of usage.

A filter 9 which prohibits passage of the treatment agent 10 is disposed between the treatment chamber 7 and the outflow canal 5. Providing such a filter permits only the treatment subject that has been brought into contact with the treatment agent 10 to be let out without the need of a process for separating the treatment agent 10 from the treated object.

The container 2 is formed of a translucent member, and light is radiated through the container 2 from a light source 15 disposed outside the container 2. This configuration not only simplifies the shape of the container 2 but also facilitates maintenance of the light source 15 and the container 2, including such a maintenance work as washing the container 2.

The tests were performed on HIV serving as the hazardous substance 3 according to the embodiment. As shown in Table 2, however, many viruses show properties of specifically bonding to their respective target cells in the course of infection, and for many viruses, there respectively exist retainers 13 that have amino groups and function as receptors for combining with proteins. There also are many viruses having specific antigens, against which specific antibodies are known to exist, and there exist retainers 13 to retain proteins that show specific antigenicity against said antibodies. The invention is applicable to any one of such viruses.

The invention is also applicable to any bacterium or toxin having specific antigenicity and characterized in that there is a specific antibody against its respective antigen and that there is a retainer 13 to retain the protein that shows specific antigenicity against said antibody.

With any such virus, bacterium or toxin, a given retainer 13 can easily be held through bridging molecules 12 to a base 11 having the photocatalytic ability so that the photocatalytic ability acquires the ability of selective retention of a specific hazardous substance 3.

The retainer 13 is not limited to a protein; any substance having amino groups that can bond to aldehyde groups at the ends of the bridging molecules 12 may serve as the retainer 13. If the retainer 13 is a protein and intended to retain any of a number of viruses, bacteria and toxins that have specific bonding characteristic or antigenic constitutive proteins, it is relatively easy to prepare the retainer 13, because the receptor or the antibody for selectively retaining the constitutive protein is also a protein.

Although the embodiment described above uses titanium oxide as the transition metal oxide having the photocatalytic ability, the usable metal oxides are not limited to titanium oxide; any transition metal oxide that exhibits strong oxidization ability when irradiated with light is applicable to the present invention. However, titanium oxide is preferable because of its various benefits, such as high stability and having on its surface hydroxyl groups which permit bonding of the bridging molecules 12 at room temperature under the presence of the air, in addition to the fact that the photocatalytic action of titanium oxide exhibits a very strong oxidization ability as described above. In case some other transition metal oxide or titanium oxide that does not have many hydroxyl groups on its surface is used, it should be treated with acid or the like to form hydroxyl groups on its surface before bonding of the bridging molecules 12.

The bridge portions according to the invention are not limited to bridging molecules 12 formed by using aminoalkylethoxysilane and glutaraldehyde, and any structure having the retainer 13 held on the surface of the base 11 is applicable. A structure that calls for forming bridging molecules 12 by using aminoalkylethoxysilane and glutaraldehyde and boding the retainer 13 to the bridging molecules 12 as in the case of the embodiment described above presents a problem in that it is in the unsaturated state, with double bonds, which have relatively high reactivity, being included in the bridging molecules 12. Therefore, it is desirable to stabilize the structure, in other words reduce its reactivity, by reducing the double bonds so as to saturate the compounds. This is to ensure that the hazardous substance 3 is retained in the base 11 by means of the retainer 13 which is stably secured on the base 11, so as to increase efficiency in the photocatalytic inactivation.

Although the invention is explained referring to the above embodiment, wherein the bridge portions include at the ends thereof aldehyde groups intended for bonding of the amino groups of the retainer 13, a structure where carbons at the ends of the retainer 13 bond to the bridge portions is also possible. In other words, by bonding bridge portions to the carbon atoms of a constitutive protein which is a part of an organic retainer 13 and located at the end far from the constitutive protein that is intended for specifically adsorbing or otherwise retaining a hazardous substance 3, reliable and stable retention of the hazardous substance 3 can be expected. Thus, the efficiency in inactivating the hazardous substance 3 can be increased.

Should there be a plurality of kinds of hazardous substances 3 mixed in the subject of treatment, it is recommended to, for example, secure different retainers 13, 13 to the base 11 so that these different retainers 13, 13 respectively deal with the hazardous substances 3, or connect a plurality of containers 2, 2, in series and fill them respectively with treatment agents 10 containing retainers 13 that specifically deal with the different hazardous substances 3.

The invention is applicable to not only continuous treatment, wherein the hazardous substance 3 is inactivated by irradiating the treatment subject with light in the state the treatment subject is in contact with the treatment agent 10, but also intermittent treatment which calls for bringing the treatment subject into contact with the treatment agent so as to retain the hazardous substance 3 by the retainer 13 without radiation of light, and, after completion of contact between the treatment subject and the treatment agent 10, radiating light so as to inactivate the hazardous substance 3, which has been trapped beforehand by the retention by the retainer 13. Such an intermittent treatment not only reliably inhibits denaturation of the constitutive components of the treatment subject, which may otherwise be caused by the photocatalytic action, but also prevents a part of the constitutive components of the decomposed hazardous substance 3 from peeling or otherwise becoming mixed again into the treatment subject.

Although the retainer 13 is bonded to the transition metal oxide according to the invention, an alternative arrangement, such as one that calls for providing on the surface of the base 11 consisting of glass beads or the like and boding the retainer 13 to the surface of the base 11.

The manner of bonding the retainer 13 to the transition metal oxide is not limited to the bond via the bridging molecules 12, and they may be connected in any appropriate manner, examples of which include adsorption that does not use bridging molecules 12. Furthermore, it is also possible to provide only a part of the bridging molecules 12 with a retainer 13 or bond different retainers 13 to the bridging molecules 12.

Examples of other applicable structures include one that calls for covering the transition metal oxide with the bridging molecules 12 and the retainer 13, which has the property of bonding to a transition metal oxide in a tightly packed manner so that the constitutive components of the treatment subject cannot touch the transition metal oxide. As with the embodiment described earlier, this structure ensures the reliable prevention of denaturation of the components of the treatment subjects by preventing undesirable contact of the treatment subject with the transition metal oxide.

The structure of the treatment device body 1 is not limited to one that calls for filling the container 2 with the treatment agent 10. One of the examples of other applicable structures calls for providing the container 2 with a double tube structure comprised of an outer tube and an inner tube which together form a treatment chamber 7 and disposing a light source 15 in the inner tube so as to enable the efficient irradiation of the transition metal oxide with the light from the light source 15. Other examples include one shown in FIG. 7 and those respectively shown in FIGS. 8, 9 and 10.

To be more specific, instead of the container 2 of the embodiment shown in FIGS. 1 through 6, a treatment device body 21 according to the embodiment shown in FIG. 7 has a container 23 which is formed of a translucent material in a generally tubular or cylindrical shape and divided so as to include therein a treatment chamber 7 to be filled with a treatment agent 22. A filter 9 that prohibits passage of the granular treatment agent 22 while permitting passage of the treatment subject is disposed at each end of the treatment chamber 7 of the container 23. In other words, these two filters 9, 9 divide the interior of the container 23, thereby forming the treatment chamber 7. The base 11 of the treatment agent 22 is formed of approximately spherical, translucent objects, such as glass beads. A layer of a transition metal oxide, such as titanium oxide, is formed on at least a part of the surface of the base 11. A retainer 13 is secured through bridging molecules 12 to the transition metal oxide on the surface of the base 11.

With the configuration as above, treatment is performed by irradiating the treatment agent 22 with ultraviolet emitted from a light source 15 while the treatment subject is introduced from an end of the container 23 in the same manner as the embodiment shown in FIGS. 1 through 6. To be more precise, a specific hazardous substance 3, i.e. the substance which has become mixed in the treatment substance, is selectively retained by the retainer 13, which has the specific bonding property to bond to the specific antigen of the particular hazardous substance 3, and the photocatalytic action of the ultraviolet radiated to the hazardous substance 3 subsequently inactivates the hazardous substance 3.

By using a generally tubular container 23 as described above, the embodiment shown in FIG. 7 enables the continuous flow of a treatment subject and inactivation of a hazardous substance 3 mixed in the treatment subject. Therefore, when the subject to be treated by this embodiment is blood, it is a simple matter to selectively inactivate a hazardous substance 3 in the blood while inhibiting denaturation of the components of the blood during external circulation as in the case of dialysis. Thus, the embodiment is capable of improving the productivity of treatment subjects, such as blood derivatives that are not contaminated with hazardous substances 3 and also offers improved medical treatment that uses blood or a blood derivative.

As the base 11 is formed of a translucent material and therefore prevented from shielding the light emitted by the light source 15, effective irradiation of the transition metal oxide is ensured. By thus improving the photocatalytic ability of the transition metal oxide, the embodiment enables the more efficient inactivation of the hazardous substance 3.

As is true in the embodiment shown in FIGS. 1 through 6, the embodiment eliminates the need of a process for separating the treatment agent 22 from the treated subject and thereby facilitates the formation of a structure that permits only the treatment subject that has been brought into contact with the treatment agent 22 to be discharged.

As it has been proven by Actual Example 4, the embodiment enables the further increase of the efficiency of treating a hazardous substance by increasing the surface area where the titanium oxide is provided.

The treatment ability can be improved by forming the container 23 in the shape of a spiral around the light source 15 or in the shape of a strip that is bent like an accordion, or otherwise increasing the distance traveled by the treatment subject in the area irradiated with the light from the light source 15.

The treatment device body 31 according to the embodiment shown in FIG. 8 is the same as the container 23 of the embodiment shown in FIG. 7 except that the container itself has the photocatalytic ability and ability of selectively retaining a hazardous substance 3.

To be more precise, the treatment device body 31 includes a base 32 formed of a translucent material in a generally tubular or cylindrical shape. A layer of a transition metal oxide, such as titanium oxide, is formed on nearly the entire inner surface of the base 32. By holding a retainer 13 through bridging molecules 12 onto the transition metal oxide, a treatment agent 33 for treating a hazardous substance 3 is formed. The treatment device body 31 also has a light source 15, which is adapted to radiate light and extends virtually in the axial direction of the treatment agent 33. A treatment subject is treated while it flows through the treatment agent 33.

As with the embodiment shown in FIG. 7, the embodiment shown in FIG. 8, too, enables the continuous flow of a treatment subject and inactivation of a hazardous substance 3 having become mixed in the treatment subject. Therefore, when the object to be treated by this embodiment is blood, it is a simple matter to selectively inactivate a hazardous substance 3 in the blood while inhibiting denaturation of the constitutive components of the blood during external circulation as in the case of dialysis. The embodiment is thus capable of improving the productivity of treatment subjects, including blood derivatives that are not contaminated with hazardous substances 3, and also offers improved medical treatment that uses blood or a blood derivative.

As with the embodiment shown in FIGS. 1 through 6 and the embodiment shown in FIG. 7, the embodiment eliminates the need of a process for separating the treatment agent 33 from the treated subject and thereby facilitates the formation of a structure that permits only the treatment subject that has been brought into contact with the treatment agent 33 to be discharged.

As the container itself functions as the treatment agent 33 as in the case of Actual Example 3, a treatment device according to the present embodiment is easy to produce and can easily be made compact in size and weight. In addition, as the container may have a tubular or other non-standard shape, the range of usage is expanded.

As is true in the embodiment shown in FIG. 7, the embodiment shown in FIG. 8, too, improves the treatment ability by forming the container 33 in the shape of a spiral around the light source 15 or in the shape of a strip that is bent like an accordion, or otherwise increasing the distance traveled by the treatment subject in the area irradiated with the light from the light source 15.

Figure 9:
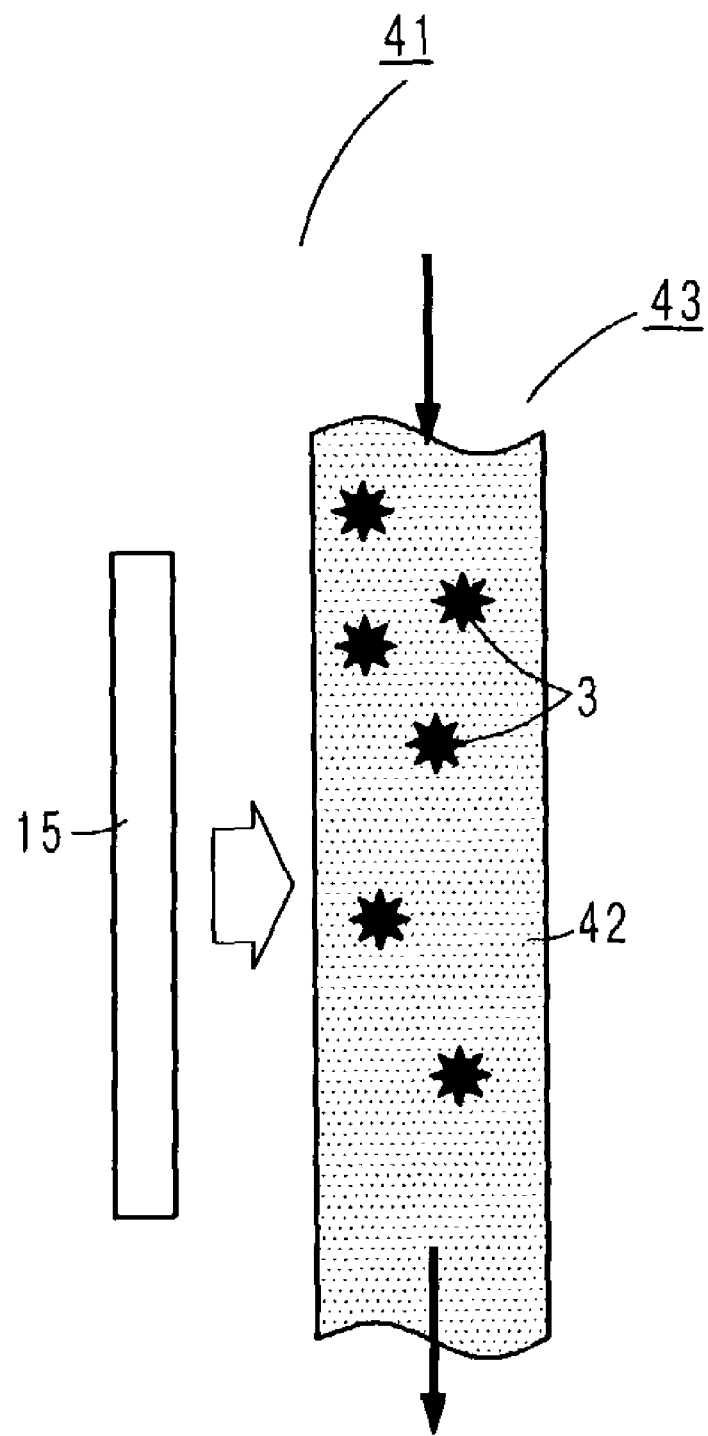
FIG. 9 is a schematic illustration to explain how the subject of treatment is treated in the main body of a treatment device according to yet another embodiment of the invention.

The treatment device body 41 according to the embodiment shown in FIG. 9 uses a porous base 42.

To be more precise, the treatment device body 41 includes a rectangular base 42 formed of a porous material having a plurality of communicating holes, i.e. contiguous pores through which the treatment subject can pass. There are no communicating holes in the outer surface of the four sides of the base member 42 so as to prevent seepage of the treatment subject.

The base member 42 may be formed, for example, to have a bumpy surface by providing ceramic particles integrally on the surface of a porous ceramic body having a three dimensional network. A photocatalytic layer principally comprised of a transition metal oxide having the photocatalytic ability, such as titanium oxide, integrally covers the bumpy surface of the base 42, i.e. the surface of the porous ceramic body and the ceramic particles thereon. A retainer 13 is held through bridging molecules 12 onto the transition metal oxide of the photocatalytic layer. Thus, a treatment agent 43 is formed.

Examples of the ceramic particles mentioned above include alumina or aluminum oxide particles having an average particle diameter in the range of 1 to 100 ìm, for example 22 ìm. Ceramic particles having an average particle diameter of less than 1 ìm are prone to making the surface of the porous ceramic body excessively smooth and reducing the ability of holding the photocatalyst and, therefore, might make it impossible to form a sufficiently stable photocatalyst coating. Coarse ceramic particles having an average particle diameter of more than 100 ìm are difficult to be stably held onto the surface of the porous ceramic body and are prone to peeling off, thereby impairing formation of a sufficiently stable photocatalyst coating. Furthermore, excessively coarse ceramic particles do not easily enter inside the porous ceramic body. As a result, the ceramic particles may be prevented from being evenly supported therein and impair formation of a uniform photocatalyst coating. Therefore, it is desirable to limit the average particle diameter of the ceramic particles supported by the porous ceramic body within the range of 1 to 100 ìm.

The porous ceramic body is formed so that the diameter of the frame that constitutes the three dimensional network is in the range of, for example, 100 to 1000 ìm. Should the diameter of the frame that forms the three dimensional network be less than 100 ìm, it may be impossible to obtain sufficiently strong filters and consequently reduce the productivity. An excessively thicker frame having a diameter of more than 1000 ìm may prevent the light from reaching inside the porous ceramic body and reduce the photocatalytic ability of the photocatalyst, thereby inhibiting effective and efficient purification of exhaust gas. Therefore, it is desirable to limit the diameter of the frame that constitutes the three dimensional network within the range of 100 to 1000 ìm.

The treatment agent 43 is so formed as to satisfy at least one of the three conditions: the porosity is in the range of 65 to 95%; the bulk density is in the range of 0.15 to 0.60 g/cm$^3$; and the number of cells is in the range of 10/25 to 30 cells/25 mm.

A treatment agent 43 with a porosity of less than 65% may cause various problems, such as an increase in the pressure loss in the course of the flow-through of the treatment subject, which is in the form of either a liquid or a gas, a decrease in the quantity of light that reaches from the light source 15 to the inside of the treatment agent 43, and a decrease in the proportion of contact with the treatment subject, thereby reducing the efficiency in trapping the hazardous substance 3. On the other hand, a porosity of more than 95% may excessively reduce the strength of the treatment agent 43, impairing its productivity and making it inconvenient to handle. Therefore, it is desirable to limit the porosity of the treatment agent 43 within the range of 65 to 95%.

A bulk density of less than 0.15 g/cm$^3$ may excessively reduce the strength of the treatment agent 43, impairing its productivity and making it inconvenient to handle. On the other hand, a treatment agent 43 with a bulk density of more than 0.60 g/cm$^3$ may cause various problems, such as an increase in the pressure loss in the course of the flow-through of the treatment subject, a decrease in the quantity of light that reaches the inside of the treatment agent 43, and a decrease in the proportion of contact with the treatment subject, resulting in a decrease in the efficiency in trapping the hazardous substance 3. In addition, an increase in the mass makes it difficult to provide a treatment agent which is more convenient to produce or handle and, therefore, necessitates a structure that enables the firmer installation of the treatment agent. In other words, the treatment agent may become less convenient to install. Therefore, the porosity of the treatment agent 43 should be limited within the range of 0.15 to 0.60 g/cm$^3$.

When the number of cells of the treatment agent 43 is less than 10 cells/25 mm, in other words when the number of cells located on a 25 mm straight line is less than 10, this may cause various problems, such as an increase in the pressure loss in the course of the flow-through of the treatment subject, a decrease in the quantity of light that reaches the inside of the treatment agent 43, and a decrease in the proportion of contact with the treatment subject, thereby reducing the efficiency in trapping the hazardous substance 3. When the number of cells of the treatment agent 43 is more than 30 cells/25 mm, in other words when the number of cells located on a 25 mm straight line exceeds 30, this may excessively reduce the strength of the treatment agent 43, impairing its productivity and making it inconvenient to handle. Therefore, it is desirable to limit the number of cells within the range of 10 to 30 cells/25 mm.

When the treatment agent 43 satisfies all the conditions described above, it presents a light transmittance in the range of 10 to 50% at a thickness of 5 mm.

The process of producing the base 42 of the treatment agent 43 described above is now explained. First, a slurry is prepared by mixing together fine ceramic powder, a binder and an appropriate quantity of water while stirring the mixture. Examples of said fine ceramic powder include fine alumina powder, fine silica powder, such as fine silicon sand powder, which is silicon oxide, and fine mullite powder. The a binder is a bonding agent made of such an organic substance as dextrin, methyl cellulose, polyvinyl alcohol or the like or an inorganic substance, such as clay, sodium silicate or the like. The slurry is attached to a porous organic body having a three dimensional structure formed of, for example, urethane foam resin, by soaking in or otherwise impregnating the porous organic body with the slurry.

Next, ceramic particles are attached to the surface of the porous organic body before the slurry becomes dry. This can be executed by, for example, sprinkling ceramic particles, such as alumina particles, silica particles or mullite particles, onto the porous organic body still wet with the slurry while shaking the porous organic body. Thereafter, the slurry is dried and baked to burn off the porous organic body and sinter the fine ceramic powder, which constitutes the slurry, and the ceramic particles into an integral body so that the ceramic particles are integrally secured to the surface of the porous ceramic body, which has been formed as a result of sintering of the fine ceramic powder.

With the ceramic particles fixed thereto, the porous ceramic body has a bumpy surface. The porous ceramic body is then soaked in a slurry containing fine titanium oxide powder or a similar substance as the principal component and an organic or inorganic binder so as to attach the slurry to the porous ceramic body. Thereafter, the porous ceramic body is dried and baked so that a film of titanium oxide is baked onto the surface of the porous ceramic body. With a photocatalytic layer being thus formed, the formation of the base 42 is completed.

When treatment is performed by passing a treatment subject through the treatment agent 43, the treatment subject does not flow straight; it winds through the cells of communicating holes, which are communicating pores constituting the meshes of the three dimensional network, while frequently repeating turbulence, such as contraction flow or changes of direction. As a benefit of the configuration described above, the proportion of contact between the hazardous substance 3 contained in the treatment subject and the retainer 13 of the treatment agent 43 is increased so that the retainer 13 retains the hazardous substance 3 more efficiently. The hazardous substance 3 thus retained is inactivated by photocatalytic decomposition.

As described above, the embodiment shown in FIG. 9, wherein a porous treatment agent 43 is used, increase the contact proportion between the treatment subject and the retainer 13, facilitates the formation of a structure adapted to treat a treatment subject while the treatment subject flows through the treatment agent. The embodiment shown in FIG. 9 thus enables the more efficient inactivation of the hazardous substance 3.

As with the embodiment shown in FIGS. 1 through 6 and the embodiments shown in FIGS. 7 and 8 respectively, the embodiment of FIG. 9 eliminates the need of a process for separating the treatment agent 43 from the treated subject and thereby facilitates the formation of a structure that permits only the treatment subject that has been brought into contact with the treatment agent 43 to be discharged.

Figure 10:
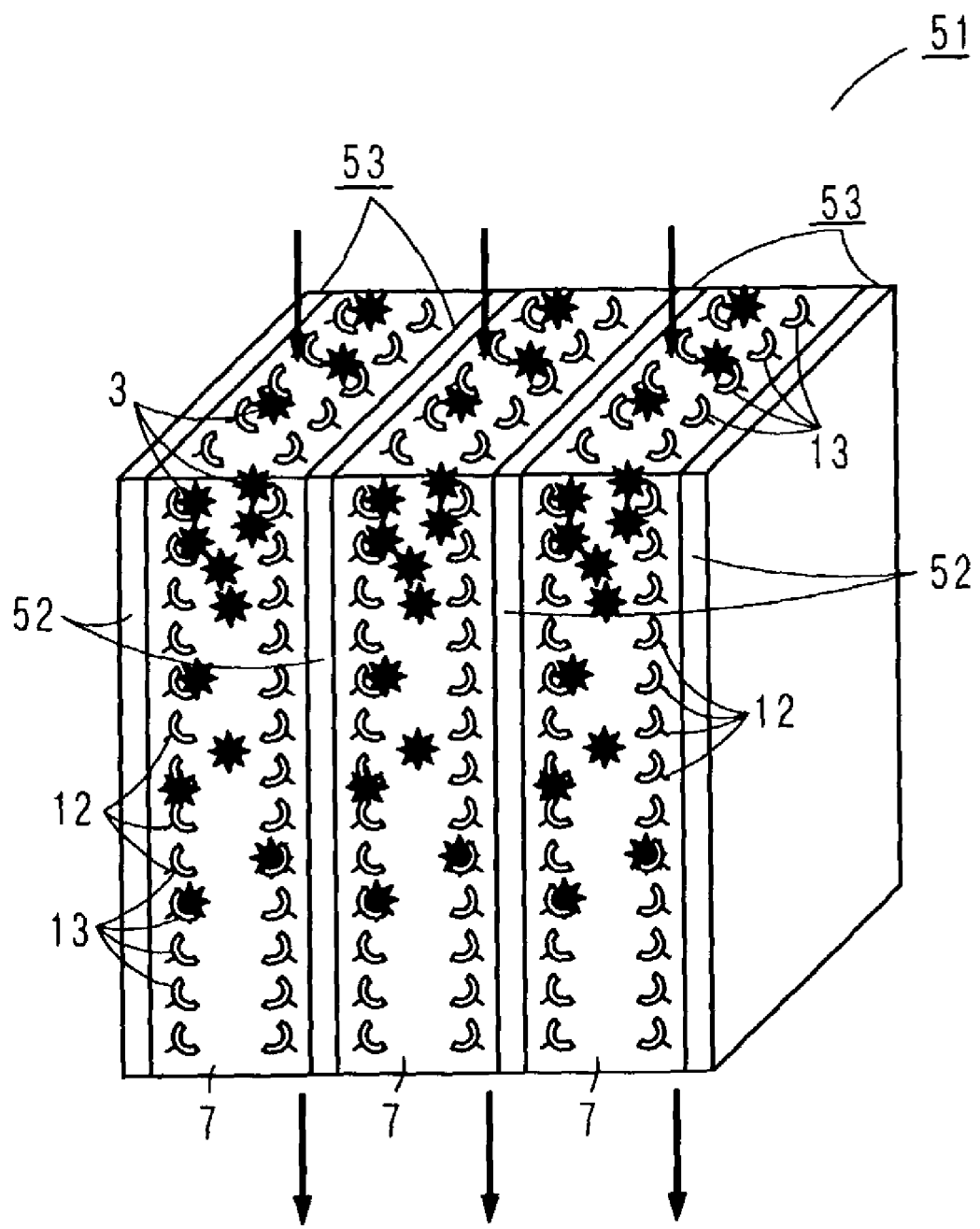
FIG. 10 is a schematic illustration to explain how the subject of treatment is treated in the main body of a treatment device according to yet another embodiment of the invention.

The treatment device body 51 according to the embodiment shown in FIG. 10 has a plurality of treatment chambers 7, 7.

The treatment device body 51 has base members 52 which consist of light guiding plates for guiding the light emitted by a light source (not shown). A layer of titanium oxide or any other appropriate transition metal oxide having the photocatalytic ability is formed on the side faces of each base member 52. A retainer 13 is held through bridging molecules 12 onto each layer of the transition metal oxide. Thus, a plurality of treatment agent members 53 are formed. These treatment agent members 53 are arranged parallel to one another at given intervals so that the space between each treatment agent member 53 and its adjacent treatment agent member 53 defines each respective treatment chamber 7.

By means of the plurality of treatment chambers 7, 7, the embodiment shown in FIG. 10 enables the more efficient inactivation of the hazardous substance 3.

Although a plurality of treatment chambers 7, 7 are provided, the light guiding plates enables the radiation of light to the transition metal oxide facing each treatment chamber 7 located inside the treatment device body 51, thereby facilitating the formation of a structure which calls for providing a plurality of treatment chambers 7, 7 to increase the treatment efficiency.

The embodiment is capable of coping with cases where the treatment subject containing different hazardous substances 3 by providing different kinds of retainers 13 that are respectively intended for said different hazardous substances 3 and positioning each type of retainer 13 so as to face each respective treatment chamber 7. As there is no need of arranging a plurality of treatment chambers 7, 7 in series, the treatment device can easily be made compact.

By specifically retaining a particular hazardous substance in a treatment subject by a retainer and inactivating the retained hazardous substance by the photocatalytic function of a transition metal oxide, the present invention is capable of efficiently inactivating a specific hazardous substance while inhibiting photocatalytic denaturation of the constitutive components of the treatment subject, thereby increasing the efficiency in treating the hazardous substance.

Possible Industrial Application

The range of usage of a treatment agent, a method, and a device for treating a hazardous substance according to the present invention includes removing toxins or biologically hazardous organisms, such as viruses or pathogenic bacteria, from blood, a blood derivative or other similar material containing such hazardous substances by inactivating the hazardous substances.

TABLE 2

| Virus | Receptor | Disease |
|---|---|---|
| Herpesviridae | | |
| herpes simplex virus | neuron surface antigen | encophalitis |
| Hepadonaviridae | | |
| hepatitis B virus | hepatocellular surface antigen | hepatitis, hepatoma |
| Picornaviridae | | |
| poliovirus | neuron surface antigen | encephalitis, myelitis |
| Togaviridae | | |
| alpha virus | neuron surface antigen | encophalitis |
| Flaviviridae | | |
| yellow fever virus | hepatocellular surface antigen | acute liver failure, hemorrhage |
| hepatitis C virus | hepatocellular surface antigen | hepatitis, hepatoma |
| Rhabdoviridae | | |
| Rabies virus | neuron surface antigen | encephalitis, myelitis |
| Filoviridae | | |
| Marburg virus | hepatocellular surface antigen | acute liver failure, hemorrhage |
| Ebola virus | hepatocellular surface antigen | acute liver failure, hemorrhage |
| Arenaviridae | | |
| Lassa fever virus | pulmonary/hepatic/neural cell surface antigen | interstitial pneumonia, hepatitis, encephalitis, hemorrhage |
| Bunyaviridae | | |
| Crimean-Congo hemorrhagic fever virus | pulmonary/hepatic/renal cell surface antigen | pneumonia, hepatitis, nephritis, hemorrhage |

TABLE 2-continued

| Virus | Receptor | Disease |
|---|---|---|
| HFRS virus*1 | pulmonary/hepatic/renal cell surface antigen | pneumonia, hepatitis, nephritis, hemorrhage |
| Retroviridae | | |
| human immunodeficiency virus (HIV) | T cell surface CD4 antigen | acquired immunodeficiency syndrome |

*1 HFRS: hemorrhagic fever with renal syndrome

TABLE 3

[Toxins]

| Name of Toxin | Producer | Disease | Antibody |
|---|---|---|---|
| endotoxin | Gram negative bacteria | endotoxin shock, disseminated intravascular coagulation (DIC) | anti-endotoxin antibody |
| verotoxin | E-coli O157 | enterohemorrhage, hemolytic uremic syndrome | anti-verotoxin antibody |
| á-toxin | staphylococcus aureus | skin necrosis, hemolysis | anti-á-toxin antibody |
| leucocidin | staphylococcus aureus | destruction of white blood cells | anti- leucocidin antibody |
| enterotoxin (SEA, SEB) | staphylococcus aureus | food poisoning, atopic dermatitis | anti-endotoxin antibody |
| exfoliative toxin | staphylococcus aureus | SSSS*2 | anti- exfoliative toxin antibody |
| toxic shock syndrome toxin (TSST) | staphylococcus aureus | shock | anti-TSST antibody |
| streptococcal toxic shock syndrome toxin (STSS) | group A streptococcus | shock | anti- STSS antibody |
| botulinum toxin | botulinus bacillus | flaccid paralysis | anti- botulinus (A-G) antibody |
| tetanospasmin | tetanus bacillus | spastic paralysis | anti- tetanospasmin antibody |
| diphtheria toxin | diphtheria bacillus | cardiac paralysis, paralysis of peripheral vascular motoneuron | anti- diphtheria toxin (A,B) antibody |

*2 SSSS: staphylococcal scalded skin syndrome

The invention claimed is:

1. A hazardous substance treatment agent including:
   a retainer having the specificity of retaining only a specific hazardous substance that has become mixed in or has the possibility of becoming mixed in a treatment subject that is in at least either a liquid or gaseous phase, wherein said retainer has amino groups or is a protein, and
   a transition metal oxide for inactivating by a photocatalytic action the hazardous substance retained by said retainer.

2. A hazardous substance treatment agent according to claim 1, wherein:
   the retainer is attached to the transition metal oxide.

3. A hazardous substance treatment agent according to claim 1, wherein:
   the hazardous substance treatment agent includes a base, on which at least a part of the surface is provided with said transition metal oxide.

4. A hazardous substance treatment agent according to claim 3, wherein:
   the base is formed of a translucent material.

5. A hazardous substance treatment agent according to claim 1, wherein:
   the retainer has amino groups, and
   the treatment agent includes bridge portions that are intended to bond to the transition metal oxide and include at the ends thereof aldehyde groups for bonding to said amino groups.

6. A hazardous substance treatment agent according to claim 5, wherein:
   the bridge portions are formed by bonding aminoalkylethoxysilane to the transition metal oxide, and bonding glutaraldehyde to the amino groups of said aminoalkylethoxysilane bonded to the transition metal oxide.

7. A hazardous substance treatment agent according to claim 5, wherein:
   the transition metal oxide has on the surface thereof hydroxyl groups intended for bonding to the bridge portions.

8. A hazardous substance treatment agent according to claim 1, wherein:
   the retainer is a protein, and
   the treatment agent includes bridge portions intended to bond to the transition metal oxide and including at the ends thereof aldehyde groups for bonding to amino groups that constitute a protein.

9. A hazardous substance treatment agent according to claim 6, wherein:
   the bridge portions are formed by reducing the double bonds that bond the aminoalkylethoxysilane with the glutaraldehyde and the glutaraldehyde with the retainer, after bonding of the retainer.

10. A hazardous substance treatment agent according to claim 1, wherein:
    the transition metal oxide is provided such that it is prevented from coming into contact with the treatment subject.

11. A hazardous substance treatment agent according to claim 1, wherein:
    the retainer covers the transition metal oxide.

12. A hazardous substance treatment agent according to claim 1, wherein:
    the hazardous substance treatment agent is formed in the shape of powder or granular particles.

13. A hazardous substance treatment agent according to claim 1, wherein:
the hazardous substance treatment agent is formed in a tubular shape so as to permit a treatment subject to pass through the inside of the hazardous substance treatment agent.

14. A hazardous substance treatment agent according to claim 1, wherein:
the hazardous substance treatment agent is formed in a porous shape having a plurality of communicating pores which a treatment subject can pass through.

15. A hazardous substance treatment agent according to claim 1, wherein:
the hazardous substance is a virus, a bacterium or a toxin and has a constitutive protein that has specific antigenicity.

16. A hazardous substance treatment agent according to claim 1, wherein:
the transition metal oxide is titanium oxide.

17. A hazardous substance treatment device including:
a hazardous substance treatment agent according to claim 1, and
a light source for irradiating the transition metal oxide of said hazardous substance treatment agent with light.

18. A hazardous substance treatment device according to claim 17, wherein:
the hazardous substance treatment agent is formed in the shape of powder or granular particles, and
the hazardous substance treatment device includes a container which is adapted to contain said hazardous substance treatment agent and provided with:
an inflow port to introduce the treatment subject into the container and
outlets that permit passage of said treatment subject while prohibiting passage of the treatment agent.

19. A hazardous substance treatment device according to claim 17, wherein:
the light source is adapted to radiate light having a wavelength ranging from visible light to ultraviolet.

20. A hazardous substance treatment agent having:
a selective retaining function based on amino groups or protein to retain only a specific hazardous substance that has become mixed in or has the possibility of becoming mixed in a treatment subject that is in at least either a liquid or gaseous phase, and
a photocatalytic function that inactivates the hazardous substance retained by said selective retaining function.

21. A hazardous substance treatment method which calls for:
a hazardous substance treatment agent that has:
a retainer having the specificity of retaining only a specific hazardous substance and
a transition metal oxide having the photocatalytic ability to inactivate a hazardous substance retained by said retainer, wherein said retainer has amino groups or is a protein, wherein said method comprises:
bringing a treatment subject, which is in at least either a liquid or gaseous phase and in which said hazardous substance is either contained or presents the possibility of becoming mixed, into contact with said treatment agent, and
irradiating said transition metal oxide with light.

22. A hazardous substance treatment method according to claim 21, wherein:
said light is radiated to the hazardous substance treatment agent after the treatment subject is in contact with said hazardous substance treatment agent for a given period of time.

* * * * *